United States Patent [19]

Glamkowski et al.

[11] Patent Number: 4,847,414

[45] Date of Patent: Jul. 11, 1989

[54] 2'-SUBSTITUTED-SPIRO[BENZOFURAN-2(3H),1'-CYCLOHEXANES] AND INTERMEDIATES THEREOF

[75] Inventors: Edward J. Glamkowski, Warren; Michael C. Jones, Somerville, both of N.J.

[73] Assignee: Hoechst-Roussel Pharmaceuticals, Inc., Somerville, N.J.

[21] Appl. No.: 471,404

[22] Filed: Mar. 2, 1983

Related U.S. Application Data

[62] Division of Ser. No. 313,097, Oct. 19, 1981, Pat. No. 4,404,221.

[51] Int. Cl.$^4$ ............................................. C07C 87/28
[52] U.S. Cl. ..................................... 564/338; 564/307
[58] Field of Search ............... 564/308, 336, 337, 338, 564/339

[56] References Cited

U.S. PATENT DOCUMENTS

| | | | |
|---|---|---|---|
| 3,470,249 | 9/1969 | Frankus et al. | 564/339 X |
| 3,652,769 | 3/1972 | Saari | 564/305 X |
| 3,974,157 | 8/1976 | Shetty et al. | 564/339 X |

OTHER PUBLICATIONS

Casy et al., "Jorn. Chem. Soc. London", pp. 3635–3638 (1964).

Primary Examiner—Robert V. Hines
Attorney, Agent, or Firm—Tatsuya Ikeda

[57] ABSTRACT

2'-substituted-spiro[benzofuran-2(3H),1'-cyclohexanes] and methods of preparing same are described. On the aromatic portion of the benzofuran ring, there may be a substituent or substituents including halogen, amino, lower-alkyl-substituted amino, lower alkyl, lower alkoxy, hydroxy and nitro. The substituents at the 2-position of the cyclohexane ring are —$(CH_2)_nNR^1R^2$ where n is 0, 1 or 2 and $R^1$ and $R^2$ are each independently hydrogen and alkyl of 1–3 carbons. These compounds are useful as antidepressants and analgesics.

Various other compounds which are useful as intermediates for preparing the aforementioned compounds and methods for preparing same are also described.

25 Claims, No Drawings

2'-SUBSTITUTED-SPIRO[BENZOFURAN-2(3H),1'-CYCLOHEXANES] AND INTERMEDIATES THEREOF

This is a division of application Ser. No. 313,097 filed Oct. 19, 1981 and now U.S. Pat. No. 4,404,221.

DESCRIPTION OF THE INVENTION

This invention relates to 2'-substituted-spiro[benzofuran-2(3H),1'-cyclohexanes] of the general formula

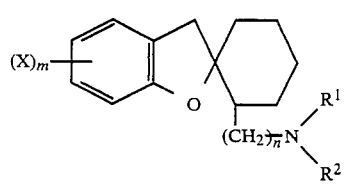

wherein X is hydrogen, halogen (F, Cl, Br, and I), amino, lower-alkyl-substituted amino, lower alkyl, lower alkoxy, hydroxy and nitro; m is an integer of 1, 2 or 3, X being the same or different when m is larger than 1; n is an integer of 0, 1 or 2; and $R^1$ and $R^2$ are each independently hydrogen and alkyl of one to three carbons; to methods of synthesizing said compounds; to methods of treatment with pharmaceutically effective amounts thereof; and to pharmaceutical compositions containing such compounds as active ingredients.

This invention also relates to intermediate compounds of the general formula

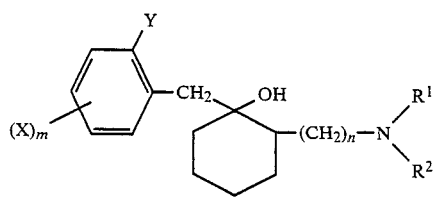

where X, $R^1$ and $R^2$ are the same as defined in formula I and n is an integer of 0 or 1, and Y is chlorine, bromine or preferrably fluorine, and to methods of synthesizing same.

This invention further relates to various compounds derived from compounds of formula II which are useful intermediates for compounds of formula I, and to methods of synthesizing same.

To the best of our knowledge, the compounds of this invention have not heretofore been made, used, described or suggested.

Unless otherwise stated or indicated, the term "alkyl" as used throughout the specification and appended claims refers to methyl, ethyl and n-propyl groups. Similarly, the term "alkoxy" refers to methoxy, ethoxy and n-propyloxy groups.

Unless otherwise stated or indicated, a given structural formula or nomenclature for the spiro[benzofuran-2(3H),1'-cyclohexane] derivatives and the cyclohexanol derivatives of this invention shall subsume all stereoisomers thereof.

Unless otherwise stated or indicated, the term "halogen" as used herein includes fluorine, chlorine, bromine and iodine.

The compounds of the present invention are prepared in the following manner. The substituents X, Y, $R^1$ and $R^2$ and the members m and n are as defined previously.

The intermediate compounds of the general formula

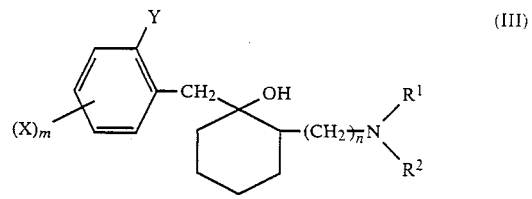

where X is hydrogen or halogen, Y is chlorine, bromine or preferably fluorine and $R^1$ and $R^2$ are each independently hydrogen or alkyl and n is 0 or 1, are synthesized by first reacting a halide of the general formula

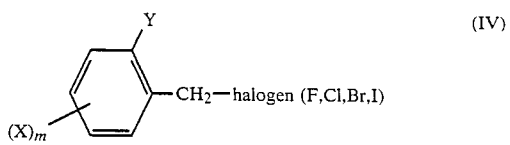

where X is as defined in formula III, with a metal, e.g. lithium, magnesium, etc., and then reacting the resulting organometallic reagent or Grignard reagent with a compound of the general formula

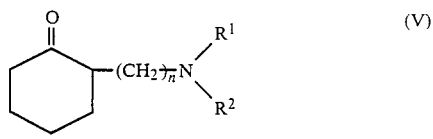

where $R^1$ and $R^2$ are as defined in formula III, to form compounds of the invention having the formula

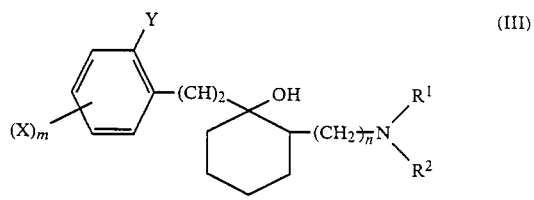

including the stereoisomers thereof, e.g. when n=1,

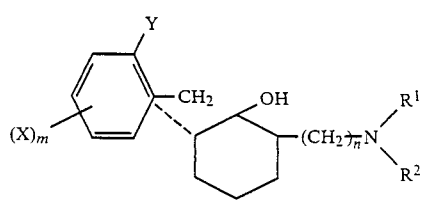

[cis, II(a)]

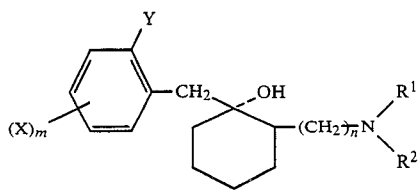

[trans, II(b)]

Alternatively, an organometallic compound of the general formula

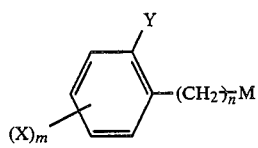

where M is a metal, for example Li, Na, K, etc. can be prepared utilizing conventional methods and reagents and in turn reacted with compound V to form compound III of the invention.

The starting ortho-halobenzylhalides of formula IV are well-known to the art and the organometallics of formula IV(a) may easily be prepared therefrom utilizing conventional techniques, e.g. by metal-halogen exchange. The starting ketones of formula V are also known to the art. In this regard reference is made to K. Flick et al. Arzneim.-Forsch., 28 107 (1978).

The spiro compound of the general formula

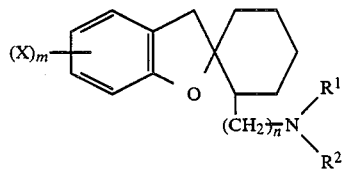

where X and R are as previously defined in formula III is obtained by a conventional ring closure of compounds II in the presence of a strong base, such as for instance, sodium hydride, phenyllithium, etc. The cis and trans stereoisomer of compound VI are obtained respectively from the cis and the trans isomers of compound III. Thus, for example, where n=1, compound II(a) would yield

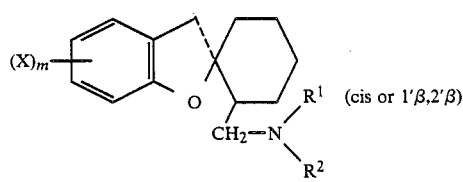

compound III(b) would yield (trans or 1'α,2'β)[VI(b)]

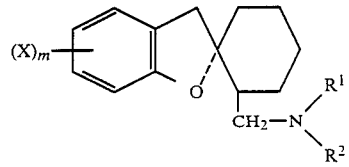

The description of cis-isomers or 1'β, 2'β isomers of the compounds VI means that the oxygen atom of the benzofuran group and the methylene group attached to the amino group are both above the average plane of the six-membered cyclohexane ring. The description of transisomers or 1'α, 2'β isomers of the compounds VI means that either the oxygen atom of the benzofuran group or the methylene group attached to the amine group is above the average plane while the other is below the average plane of the six-membered cyclohexane ring.

Once the spiro compound VI is obtained, one can obtain many derivatives thereof having a substituent or substituents of various types on the aromatic portion of the benzofuran ring, namely, compounds of the general formula

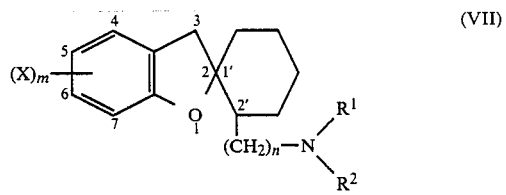

where $R^1$ and $R^2$ are as defined in formula III; X is hydrogen, halogen, amino, alkyl-substituted amino, alkyl, alkoxy, hydroxy and nitro; and m is an integer of 1, 2 or 3, X being the same or different when m is larger than 1 and n is an integer of 0 or 1.

Compound VI where X is hydrogen, is treated in a conventional manner to obtain a halide compound where X is a halogen. Typically, compound VI is treated with a halogen, e.g. chlorine, bromine, in the presence of a conventional catalyst, e.g. ferric halides, aluminum halides, transition metal halides, iodine aluminum amalgam or such reagents as iodine monochloride and iodine monobromide, silver sulfate plus iodine in sulfuric acid, trifluoroacetylhypoiodate, iodine plus peracetic acid in acetic acid, etc., to obtain a halogen substituted compound VII of the invention where X is Br, Cl or I. Preferably, compound VI is reacted with N-bromosuccinimide (NBS) or N-chlorosuccinimide (NCS) or iodine monochloride to obtain compound VII mono-substituted in the 5-position, di-substituted in the 5, 7 positions, and trisubstituted in the 5,6,7 positions.

It is to be noted that the polybromination of compound VI with NBS is facilitated by the coexistence with NCS in the reaction. Additionally, the 5-bromo-7-chloro compound is obtained by chlorinating compound VII, where X is bromine at the 5-position, with a suitable amount of NCS. The 7-chloro compound in turn is then obtained by reacting the 5-bromo-7-chloro compound with an alkyl lithium or phenyl lithium in a suitable solvent and then hydrolyzing the resultant product with water.

The mono-halide compound VII, where X is a halide, e.g. the 5-bromo compound, is reacted with an alkyl metal compound, e.g. n-butyllithium, in a suitable solvent to form an organometallic compound of the formula

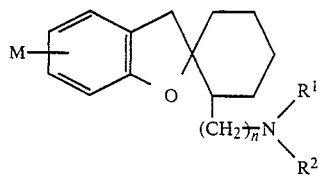 (VIII)

where M is a metal, e.g. Li. Compound VIII in turn is reacted with an alkyl halide or alkyl sulfate, e.g. dimethyl sulfate, in a conventional manner to form compound VII of the invention wherein X is alkyl, e.g. methyl.

Compound VII, where X is a halogen, e.g. 5-bromo, is reacted with an alkaline metal alkoxide, e.g., alkaline metal methoxide, and cuprous iodide, to form compound VII of the invention where X is alkoxy, e.g. methoxy. This resultant compound in turn can be dealkylated, using conventional techniques to form compound VII of the invention where X is hydroxy. Typically, the formation of hydroxyl is carried out by cleavage with basic reagents, e.g. NaOH, Grignard reagents, sodium and butanol, sodium in liquid ammonia, lithium salt of diphenylphosphine, etc., or by acid cleavage with reagents such as hydrogen bromide, hydrogen iodide, hydrogen iodide plus phosphorus, potassium iodide plus phosphoric acid, pyridine hydrochloride, boron tribromide, anhydrous aluminum chloride, etc. Preferably the pyridine-hydrogen chloride complex is employed to achieve the formation of compound VII where X is OH.

Preferably, for the purpose of nitrating compound VI, where X is hydrogen, it is advantageous to first convert the

group to

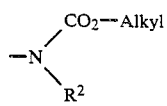

by use of an alkyl haloformate, e.g. ethylchloroformate. This prevents the oxidation of the basic

group during nitration, as for example with nitric acid. The resultant alkyloxycarbonyl group, e.g. ethoxycarbonyl group, thus introduced can subsequently be converted to a methyl group by use of a conventional reducing agent such as LiAlH$_4$. Compound VI is typically reacted with an alkyl chloroformate to form compound IX of the formula

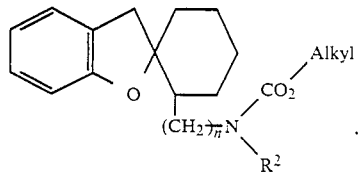 (IX)

which in turn is nitrated, in a conventional manner, e.g. with nitric acid in glacial acetic acid, to form a compound having the formula

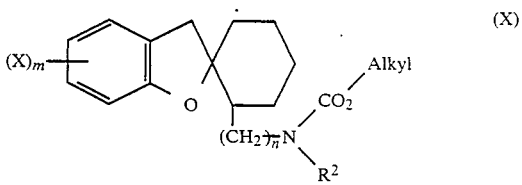 (X)

where X is nitro. Compound X e.g., the 5-nitro compound, is reduced in a conventional manner, such as by treatment with a metal and acid; catalytically with hydrogen and Pt, Pd, etc; sodium hydrosulfite, etc., to a compound having the formula

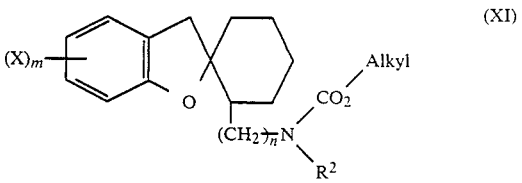 (XI)

where X is —NH$_2$. The N-alkyl derivative of the amine XI is obtained in a conventional manner, as by reaction with an alkyl halide, e.g. methyl halide, whereby a mono- or bi-substituted compound is obtained,

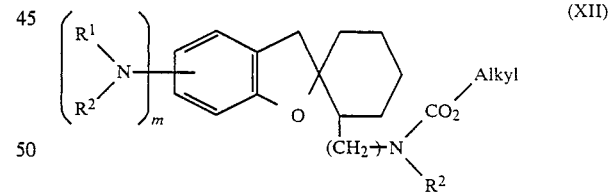 (XII)

Typically, for example, the 5-amino compound, which is obtained by reduction of the 5-nitro compound of formula X, is reacted with a methyl halide to form a 5-methyl amimo derivative or if desired is reacted with the methyl halide in a sufficient quantity to form a 5-dimethyl amino derivatives. Alternatively, the 5-dimethyl amino derivative, for example, can be obtained by hydrogenating a mixture of formaldehyde and the 5-nitro derivative of compound X in the presence of palladium/carbon.

Compounds X, XI, and XII can be reduced by means of a reducing agent such as a metal hydride, e.g. LiAlH$_4$, etc., to form compounds VII of the invention where X is NH$_2$, and

whereby the

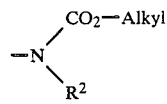

group is converted to

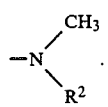

It is to be pointed out that compounds of the invention having the formula

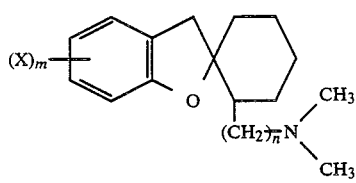 (XIII)

can be prepared by reacting compound VII where $R^1$ and $R^2$ are hydrogen with formaldehyde and formic acid, according to the Eschweiler-Clarke procedure. Spiro compounds with a N-methylaminomethyl chain (compound XIV) having the formula

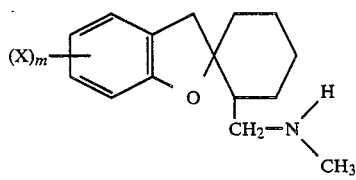 (XIV)

where X is hydrogen or halogen can be prepared from

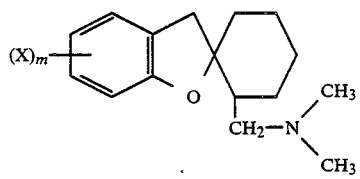 (XV)

through different routes. One is a carbamation of the compound XV with alkyl chloroformate or phenylchloroformate followed by hydrolysis of the demethylated product in the presence of alkaline metal hydroxide or alkaline earth metal hydroxide. The other method is displacement of a methyl group of the compound XV with a cyano group using, for example, cyanogen bromide followed by a reduction of the cyano compound with a conventional reducing agent such as $LiAlH_4$.

The intermediate compounds of the invention having the formula

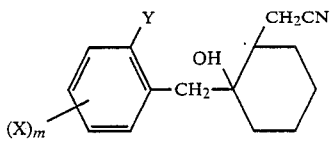 (XVI)

where X is hydrogen or halogen and Y is as defined previously, are synthesized by reacting compound IV with a suitable metal to form a Grignard reagent or an organometallic (compound IV(a)) which in turn is reacted with 2-oxo-cyclohexaneacetonitrile,

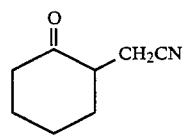

to form intermediate compounds XVI of the invention. The compound XVI can be treated with a strong base, as previously described, to effect ring closure to yield spiro compounds of the formula

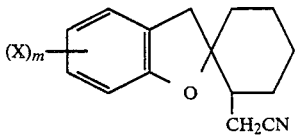 (XVII)

It is, of course, understood that the compounds discussed above include the stereoisomers thereof where they exist and such isomers fall within the scope of the invention disclosed herein. For example, compound III includes both the cis isomer III(a) and the trans isomer III(b) when n is 1. The relative proportions of the two depend on various factors, including the identity of the substituent X, the identity of the substituent R, and the reaction condition, but usually the cis isomer is favored over the trans isomer. Typical values of the proportions are 70–80% for the cis isomer and 30–20% for the trans isomer.

A preferred general procedure for separating the mixtures of the isomers of the subject invention into substantially pure isomers is the following: (i) A mixture of the isomers which typically contains 80–70% of cis isomer and 20–30% of trans isomer, as in compounds III(a) and III(b), is dissolved in ethanol. To this solution is added with stirring a solution of anhydrous oxalic acid in a suitable solvent, e.g. ethanol. The molar amount of oxalic acid should be in excess of those of the compounds, e.g. III(a) and III(b). (ii) After stirring for an extended period, e.g. about 16 hours (overnight), crystals are collected and washed with a suitable solvent or solvents such as ethanol and ether. A much purer oxalate salt of the cis isomer is obtained. Typically a cis oxalate of about 90% isomeric purity is obtained in this step. (iii) The cis oxalate obtained in step (ii) is recrystallized from a suitable solvent, e.g. ethanol once or twice. This affords almost 100% pure cis oxalate. The free base of the cis isomer is liberated by reacting the oxalate with a base such as potassium hydroxide.

The mother liquor remaining after step (ii) is richer in the trans isomer than the starting mixture. The trans isomer is purified by chromatography of the free base or by recrystallization of the salt, such as the oxalate salt and/or the hydrochloride salt.

It is, of course, understood that any conventional method of separating and purifying stereiosomers can be employed and the invention is not to be limited by any such particular method.

Compounds VII where n is 2 can be prepared in the following manner. Compound XVII is reduced, by any conventional means, e.g., hydrogen plus a metal catalyst, such as Pd, Pt etc., or with a metal hydride, such as LiAlH$_4$, to obtain a spiro compound of the formula

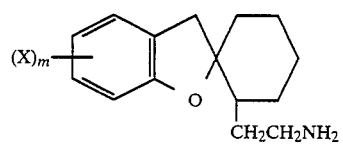

(XVIII)

where X is hydrogen or halogen.

The N-alkyl derivatives of compound XVIIII are prepared in a conventional manner, as for example by reaction with an alkyl halide compound whereby a mono- or bi-substituted compound is obtained,

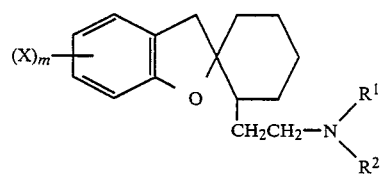

(XIX)

where at least R$^1$ or R$^2$ is alkyl.

Alternatively, compound XVIII can be reacted with an alkyl chloro formate followed by reduction of the resultant compound, as with LiAlH$_4$, to form compound (XIX).

Compound XIX where R$^1$ and R$^2$ are methyl is obtained, by hydrogenating a mixture of formaldehyde and compound XVIII in a conventional manner, e.g. in the presence of palladium or platinum on carbon.

Once the spiro compound XVII is obtained, where X is hydrogen or halogen, one can obtain many derivatives thereof having various substituent or substituents on the aromatic portion of the benzofuran ring, where X is hydrogen, halogen, amino, alkyl-substituted amino, alkyl, alkoxy, hydroxy and nitro and m is an integer of 1, 2 or 3, X being the same or different when m is larger than 1. The synthetic procedures used for this purpose are much the same as those used deriving compounds of the formula VII where n is 0 or 1, described above.

Again it is to be understood that stereoisomers of compound VII where n is 0, 1 or 2 are included within the scope of the invention described herein.

The compounds (I) of the present invention are useful in the treatment of depression in mammals, as demonstrated by their ability to inhibit tetrabenazine-induced depression in mice (International Journal of Neuropharmacology, 8, 73 (1967), a standard assay for useful antidepressant properties. The compounds I are further useful as analgesics. The procedure employed here for evaluating the analgesic activities of the compounds I is a modification of Siegmund et al. Proc. Soc. Exptl. Biol. Med., 95 729 (1957). Thus, 12.5 mg of phenylquinone (phenyl-p-benzoquinone) is dissolved in 5 ml of 95% ethanol and diluted to 100 ml with distilled water and administered to mice (10 ml/kg, i.p.). This produces a characteristic "writhe" which is defined as an inward rotation of one or more feet with twisting and turning of the trunk, drawing in of the abdominal wall, lorodis and arching of the back.

A total of 28 male, CD-1 mice (18 to 30 grams) are employed for a time response. Animals receive food and water ad libitum. Drugs to be tested are prepared with distilled water, and if insoluble, one drop of a suitable surfactant is added.

Twenty animals (5/group) are administered the drug subcutaneously (sc) 15, 30, 45 and 60 minutes prior to phenylquinone injection. Control animals (2/group) receive an equal amount of vehicle. After the administration of phenylquinone, the mice are placed separately into one-liter beakers and 5 minutes are allowed to elapse. The mice are then observed for a period of 10 minutes and the number of writhes are recorded for each animal. The formula for computing percent inhibition is:

$$\frac{x \text{ Writhes in Conrtol Group} - x \text{ Writhes in Drug Group}}{x \text{ Writhes in Control Group}} \times 100$$

The time period with the greatest percent of inhibition is considered the peak time.

A dose range is run in the same fashion as a time response except ten animals per group are tested at the peak time of drug activity. Fifty animals, four drug groups, and a vehicle control are employed. Animals are dosed and tested in a randomized manner. An estimated ED$_{50}$ is calculated by a computer linear regression analysis.

The antidepressant and analgesic activities of various spiro compounds having the formula

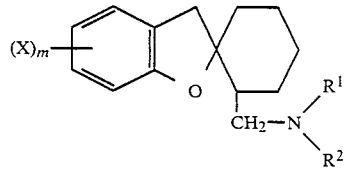

where X is hydrogen, chlorine or bromine and m is 1 or 2, taken as representative of a loer class of compounds having the formula I are presented in Table 1. The data presented therein were determined in accordance with the above described procedures.

Table 1. Pharmacological data of compounds having the formula

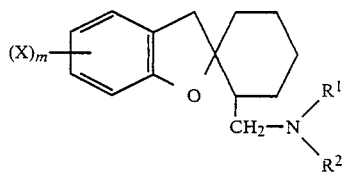

1. Antidepressant activity (as measured by inhibition of tetrabenazine induced ptosis).

| Chemical Structure | | | ED$_{50}$ |
|---|---|---|---|
| (X)$_m$ | R | Isomer | (mg/kg,po) |
| 5-chloro | Me | cis | 1.5 |

-continued

| Chemical Structure | | | $ED_{50}$ |
|---|---|---|---|
| $(X)_m$ | R | Isomer | (mg/kg,po) |
| 5-chloro | Et | cis | 4.73 |
| H | Me | trans | 3.0 |
| 5-chloro | Me | trans | 1.39 |
| 4-chloro | Me | trans | 5.7 |
| 6-chloro | Me | trans | 0.42 |
| 5-bromo | Me | cis | 4.73 |
| 5,6-dichloro | Me | cis | 3.46 |

2. Analgesic activities (as measured in the phenylquinone writhing test).

| Chemical Structure | | | $ED_{50}$ |
|---|---|---|---|
| $(X)_m$ | R | Isomer | (mg/kg,sc) |
| H | Me | cis | 5.98 |
| 5-chloro | Me | cis | 4.96 |
| H | Me | trans | 2.9 |

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. The preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains 1.0 to 300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin; and a flavoring agent such as peppermint, methyl salicylate, or orange flavoring. When the dosage unit is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain a pharmaceutically effective amount, i.e. at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The invention is illustrated by the following examples wherein unless indicated otherwise, the temperature indicated is in degrees Centigrade.

EXAMPLE 1

(a)

cis-2-(Dimethylaminomethyl)-1-(2-fluorobenzyl)-cyclohexan-1-ol Oxalate

To a stirred mixture, under $N_2$, of 2.47 g of magnesium turnings and 20 ml of ether was added dropwise a solution of 14.5 g of 2-fluorobenzyl chloride in 50 ml of ether. When the first few mls. were charged, reaction began to take place spontaneously bringing the ether to reflux. The rate of addition was such as to maintain this gentle reflux (0.5 hr.). When the Grignard reaction was complete the mixture was cooled and kept at 20° C. during the slow (45 min) addition of a solution of 12.4 g of 2-dimethylaminomethylcyclohexanone in 25 ml of ether. After 3 hr. the reaction was cooled and kept at 0° while being quenched by addition of sat'd. ammonium chloride solution. Water was then added to dissolve the salts, the ether phase was separated and washed with sat'd. $NH_4Cl$, twice with dilute brine, dried over $Na_2SO_4$, and concentrated to an oil weighing 19.3 g (91%)).

An estimation from TLC indicated this consisted of a 4:1 cis:trans ratio of alcohols which were separated via the oxalate salt. To this end, the oil was dissolved in ethanol, with stirring, and then a solution of 9.1 g anhydrous oxalic acid in ethanol was added. After stirring overnight, crystals consisting of a much purified cis alcohol salt were collected. Recrystallization from ethanol afforded the pure cis alcohol oxalate salt cis-2-(Dimethylaminomethyl)-1-(2-fluorobenzyl)cyclohexan-1-ol Oxalate m.p. 161°–164° (dec.).

ANALYSIS

Calculated for $C_{16}H_{24}FNO \cdot C_2H_2O_4$: 60.83%C, 7.37%H, 3.97%N, Found: 60.69%C, 7.43%H, 3.91%N.

(b)

trans-2-(Dimethylaminomethyl)-1-(2-fluorobenzyl)cyclohexan-1-ol Hydrochloride

Referring to Example 1(a), both the cis and trans forms of 2-(dimethylaminomethyl)-1-(2-fluorobenzyl)-cyclohexan-1-ol were prepared. The cis isomer was separated from the trans isomer by formation of an oxalate salt. The initial oxalate salt forming mother liquors from the Grignard reaction were concentrated and reversed back to the free base now rich in the trans isomer. This was adsorbed on a chromatography column containing 1.5 kg of silica gel made up in hexane. Elution with increasing percentages (10% per step) of chloroform in toluene, then with increasing percentages (1% per step) of methanol in chloroform brought forth the pure trans alcohol with 4–5% methanol in chloroform. The resulting product was dissolved in 20 ml of ethanol, and the filtered solution was treated with ethereal hydrogen chloride. The precipitated hydrochloride salt was collected to yield the pure salt (1.8 g) of trans-2-(Dimethylaminomethyl)-1-(2-fluorobenzyl)-cyclohexan-1-ol Hydrochloride, m.p. 225°–228°.

ANALYSIS

Calculated for $C_{16}H_{24}FNO \cdot HCl$: 63.67%C, 8.35%H, 4.64%N, Found: 63.91%C, 8.44%H, 4.50%N.

EXAMPLE 2

(a)

cis-1-(5-Chloro-2-fluorobenzyl)-2-(dimethylaminomethyl)-cyclohexan-1-ol Oxalate

To a stirred mixture, under $N_2$, of 2.62 g of magnesium turnings and 30 ml of ether was added dropwise a solution of 19.3 g of 5-chloro-2-fluorobenzyl chloride in 50 ml of ether. When the first few mls. were charged, reaction began to take place, spontaneously bringing the ether to reflux. The rate of addition was such as to maintain this gentle reflux (0.5 hr). When the Grignard forming reaction was complete, the mixture was cooled and kept at 15° C. during the slow (1.0 hr.) addition of a solution of 14.0 g of 2-dimethylaminocyclohexanone in 30 ml of ether. After 3 hours, the reaction was cooled and kept at 0°–10° while being quenched by addition of 150 ml of saturated ammonium chloride solution. Water was then added to dissolve the salts, the ether phase was separated and washed once with saturated $NH_4Cl$, twice with dilute brine, dried over $Na_2SO_4$, and concentrated in vacuo to an oil weighing 21.5 g (80%). An estimation from TLC indicated this consisted of a 3:1 cis:trans ratio of alcohols which were separated via the oxalate salt. To this end, the oil was dissolved in 40 ml of ethanol, with stirring, and then a solution of 8.1 g of anhydrous oxalic acid in 40 ml of ethanol was added. After stirring overnight, 11.0 g (31% yield) of crystals consisting of a much purified cis alcohol salt were collected. Recrystallization from ethanol afforded 6.8 g (19% overall yield) of cis alcohol of cis-1-(5-Chloro-2-fluorobenzyl)-2-(dimethylaminomethyl)-cyclohexan-1-ol Oxalate, m.p. 189°–191°.

ANALYSIS

Calculated for $C_{16}H_{23}ClFNO \cdot C_2H_2O_4$: 55.46%C, 6.46%H, 3.59%N, Found: 55.40%C, 6.62%H, 3.57%N.

(b)

trans-1-(5-Chloro-2-fluorobenzyl)-2-(dimethylaminomethyl)cyclohexan-1-ol

As indicated in Example 2(a), the cis isomer was separated from the trans isomer by formation of an oxalate salt. The initial oxalate salt forming mother liquors from two Grignard reactions were combined and reversed back to the free base providing 18 g rich in the trans isomer. This was adsorbed on a column containing 1.5 kg. of silica gel made up in hexane. Elution with increasing percentages (10% per step) of chloroform in toluene then with increasing percentages (1% per step) of methanol in chloroform brought forth the pure trans alcohol with 4–5% methanol in chloroform. The resulting oil crystallized to a solid (8.1 g). Recrystallization from ethanol (charcoal afforded crystals of trans-1-(5-Chloro-2-fluorobenzyl)-2-(dimethylaminomethyl)-cyclohexan-1-ol, m.p. 121°–123°.

ANALYSIS

Calculated for $C_{16}H_{23}ClFNO$: 64.10%C, 7.73%H, 4.67%N, Found: 64.13%C, 7.84%H, 4.55%N.

EXAMPLE 3

(a)

cis-1-(2,5-Difluorobenzyl)-2-(dimethylaminomethyl)cyclohexan-1-ol Oxalate

To a stirred mixture, under $N_2$, of 3.89 g of magnesium turnings in 59 ml of ether was added dropwise a solution of 26.0 g of 2,5-difluorobenzyl chloride in 75 ml of ether. When the first few mls were charged, reaction began to take place, exothermically bringing the ether to reflux. This was cooled slightly and the temperature was maintained at about 30° by adjusting the rate of addition (45 minutes). When the Grignard-forming reaction was complete, the stirred mixture was cooled and kept at 15°–20° during the slow addition (1 hour) of a solution of 21.8 g of 2-dimethylaminomethylcyclohexanone in 75 ml of ether. After 3 hours at room temperature, the mixture was cooled and kept at 0°–10° while being quenched by cautious addition of 100 ml of saturated aqueous ammonium chloride solution. Water was then added to dissolve the salts. The ether layer was separated, washed twice with dilute brine, dried over $Na_2SO_4$, and concentrated in vacuo to an oil weighing 34.3 g (86%). An estimation from TLC indicated this consisted of a 4–5:1 cis:trans ratio of alcohols. This mixture was separated via the oxalate salt. To this end, the oil was dissolved in 50 ml of ethanol and treated with a hot solution of 12.6 g of anhydrous oxalic acid in 50 ml of ethanol. After standing overnight, the crystals were collected, washed once with 35 ml of ethanol, twice with ether, and dried to afford 25.5 g (49% overall yield) of a much purified cis alcohol oxalate salt. Recrystallization from ethanol afforded 15.6 g (30% overall) of pure salt. For reference, this was recrystallized once more from ethanol to give cis-1-(2,5-Difluorobenzyl)-2-(dimethylaminomethyl)cyclohexan-1-ol Oxalate, m.p. 189°–191°.

ANALYSIS

Calculated for $C_{16}H_{23}F_2NO \cdot C_2H_2O_4$: 57.93%C, 6.75%H, 3.75%N, Found: 57.80%C, 6.83%H, 3.67%N.

(b)

trans-1-(2,5-Difluorobenzyl)-2-(dimethylaminomethyl)-cyclohexan-1-ol

As indicated in Example 3(a), the cis isomer was separated from the trans isomer by formation of the oxalate salt. The mother liquor from the salt formation, rich in the minor alcohol, was concentrated and the residue was reversed back to the free base. This material (13 g) was adsorbed on a column containing 1.5 kg of silica gel made up in hexane. Elution with increasing percentages (10% per step) of chloroform in toluene, then with increasing percentages (1% per step) of methanol in chloroform brought forth the pure isomer with 3-4% methanol in chloroform. After concentration, the resulting oil crystallized on standing, affording 8.4 g. For analysis, a sample was recrystallized (charcoal) from hexane to furnish white crystals of trans-1-(2,5-Difluorobenzyl)-2-(dimethylaminomethyl)cyclohexan-1-ol, m.p. 86°-88°.

ANALYSIS

Calculated for $C_{16}H_{23}F_2NO$: 67.82%C, 8.18%H, 4.94%N, Found: 67.76%C, 8.24%N, 4.97%N.

EXAMPLE 4

(a)

cis-1-(2-Chloro-6-fluorobenzyl)-2-(dimethylaminomethyl)cyclohexan-1-ol Oxalate

To a stirred mixture, under $N_2$, of 14.6 g of magnesium turnings and 300 ml of anhydrous ether was added dropwise a solution of 107.4 g of 2-chloro-6-fluorobenzyl chloride in 300 ml of ether. After the first charge of 25 ml, 0.1 g of iodine was added to initiate the reaction. The rate of addition and occasional cooling maintained the reaction temperature at about 30° during the 1.25 hour addition period. The mixture containing the Grignard reagent was then cooled and kept between 15°-20° during the addition over 1.25 hours of a solution of 77.6 g of 2-dimethylaminomethylcyclohexanone in 200 ml ether. After 2 hours the reaction was cooled and kept at 0°-10° while being quenched by addition of 250 ml of ammonium chloride solution. Water was then added to dissolve the salts. The aqueous phase was separated from the ether layer and reextracted with 400 ml more of ether. The combined ether layers were washed once with ammonium chloride solution, once with dilute brine, dried over anhydrous sodium sulfate, and concentrated in vacuo to an oil weighing 125 g (83%). An estimation from TLC indicated this consisted of 85:15 cis:trans ratio of alcohols. This mixture was separated via the oxalate salt by dissolving the oil (125 g) in 200 ml of ethanol, and with good stirring, adding a solution of 37.8 g of oxalic acid in 200 ml of ethanol. After 4 hours, the crystals were filtered, washed with ethanol and dried to afford 87.5 g (45% overall yield), m.p. 145°-152°. Recrystallization from ethanol provided 49.3 g (25% overall yield) of cis-1-(2-Chloro-6-fluorobenzyl)-2-(dimethylaminomethyl)-cyclohexan-1-ol Oxalate, m.p. 155°-158°.

ANALYSIS

Calculated for $C_{16}H_{23}ClFNO \cdot C_2H_2O_4$: 55.45%C, 6.46%H, 3.59%N, Found: 55.35%C, 6,61%H, 3.41%N.

(b)

cis-1-(2-Chloro-6-fluorobenzyl)-2-(dimethylaminomethyl)cyclohexan-1-ol Hydrochloride The oxalate salt of (a) above was reversed back to the pure, free base of the cis alcohol. This was dissolved in ethanol and treated with ether saturated with hydrogen chloride. The resulting HCl salt had a m.p. 205°-208°, and was formed in 23% overall yield. Recrystallization from ethanol-ether afforded the pure cis-1-(2-Chloro-6-fluorobenzyl)-2-(dimethylaminomethyl)cyclohexan-1-ol hydrochloride in 20% overall yield, m.p. 206°-208°.

ANALYSIS

Calculated for $C_{16}H_{23}ClFNO \cdot HCl$: 57.15%C, 7.19%H, 4.16%N, Found: 57.00%C, 7.22%H, 4.07%N.

(c)

trans-1-(2-Chloro-6-fluorobenzyl)-2-(dimethylaminomethyl)cyclohexan-1-ol Hydrochloride As indicated in Example 4(a) the cis isomer was separated from the trans isomer by formation of the oxalate salt. The mother liquor from this salt formation, now rich in the trans alcohol, was concentrated and the residue reversed back to the free base. This material (38.5 g) was resolved into the two pure isomers by high pressure liquid chromatography (HPLC) using an eluant of 8:1 toluene:methanol. Concentration in vacuo gave 10.5 g of the separated trans isomer as an oil which crystallized upon standing overnight. The crude trans alcohol was purified via the hydrochloride salt, which was afforded by dissolving 2.5 g of the solid in 25 ml of absolute ethanol. To the ice cold solution was added dropwise ether saturated with hydrogen chloride until the solution was acidic. The addition of 125 ml of ether produced 2.7 g (96% yield) of the crude hydrochloride salt, m.p. 203°-211° C. This was recrystallized in a 1:5, ethanol/ether mixture to give 2.3 g (85% yield) of trans-1-(2-chloro-6-fluorobenzyl)-2-(dimethylaminomethyl)-cyclohexan-1-ol Hydrochloride m.p. 209°-211° C.

ANALYSIS

Calculated for $C_{16}H_{23}ClFNO \cdot HCl$: 57.15% C, 7.19%H, 4.16%N, Found: 57.28%C, 7.26%H, 3.81%N.

EXAMPLE 5

(a)

cis-1-(4-Chloro-2-fluorobenzyl)-2-(dimethylaminomethyl)cyclohexan-1-ol Oxalate

To a stirred mixture, under $N_2$, of 20.9 g of magnesium turnings and 400 ml of anhydrous ether was added dropwise a solution of 155 g of 4-chloro-2-fluorobenzyl chloride in 400 ml of ether. After an initial charge of 25 ml, reaction began to take place, spontaneously bringing the ether to reflux. The rate of addition and occasional cooling maintained the reaction temperature at about 30° during the 1.50 hour addition period. The mixture containing the Grignard reagent was then cooled and kept between 15°-20° during the addition over 1.75 hours of a solution of 112 g of 2-dimethylaminomethylcyclohexanone in 300 ml ether. After 1 hour, the reaction was cooled and kept at 0°-10° while being quenched by addition of 500 ml of ammonium chloride solution. Water was then added to dissolve the salts. The aqueous phase was separated from the ether layer and reextracted with 500 ml more of ether. The combined ether layers were washed once with ammonium chloride solution, once with dilute brine, dried over anhydrous sodium sulfate, and concentrated in vacuo to an oil weighing 224 g (103%). An estimation from TLC indicated this consisted of a 85:15 cis:trans ratio of alcohols. The oil was dissolved in 300 ml of ethanol, and with good stirring, was treated with a solution of 64.8 g of oxalic acid in 300 ml of ethanol. After 4 hours, the crystals were filtered, washed with ethanol and dried to afford 182 g of product (65% overall yield), m.p. 175°–181°. Recrystallization twice from ethanol provided 70.8 g (25% overall) of cis-1-(4-chloro-2-fluorobenzyl)-2-(dimethylaminomethyl)-cyclohexan-1-ol oxalate, m.p. 186°–188°.

ANALYSIS

Calculated for $C_{16}H_{23}ClFNO.C_2H_2O_4$: 55.45%C, 6.46%H, 3.59%N, Found: 55.63%C, 6.43%H, 3.58%N.

(b)
Cis-1-(4-Chloro-2-fluorobenzyl)-2-(dimethylaminomethyl)cyclohexan-1-ol Hydrochloride The oxalate salt of Example 5(a) was reversed back to the pure, free base of the cis alcohol. This was dissolved in ethanol and treated with ether saturated with hydrogen chloride. The resulting HCl salt had a m.p. 219°–221°, and was formed in 23% overall yield. Recrystallization from ethanol-ether afforded the pure cis-1-(4-chloro-2-fluorobenzyl)-2-(dimethylaminomethyl)cyclohexan-1-ol hydrochloride in 21% overall yield, m.p. unchanged at 219°–221°.

ANALYSIS

Calculated for $C_{16}H_{23}ClFNO.HCl$: 57.15%C, 7.19%H, 4.16%N, Found: 57.16%C, 7.15%H, 4.17%N.

(c)
trans-1-(4-Chloro-2-fluorobenzyl)-2-(dimethylaminomethyl)cyclohexan-1-ol Hydrochloride As indicated in Example 5(a), the cis isomer was separated from the trans isomer by formation of the oxalate salt. The mother liquor from the salt formation, rich (50%) in the trans alcohol, was concentrated in vacuo and the residue was reversed back to the free base. This material (50 g) was dissolved in 100 ml of toluene and absorbed on a column containing 1.5 kg of silica gel made up on hexane. Elution with toluene, followed by increasing percentages (10% per step) of chloroform in toluene, and finally with increasing percentages (1% per step) of methanol in chloroform brought forth the pure trans isomer with 2–3% methanol in chloroform. After combining and concentrating the desired fractions, the resulting oil crystallized to a solid weighing 26.7 g. A portion of the resultant solid (8.0 g) was dissolved in 25 ml of absolute ethanol, cooled and stirred while being treated with 50 ml of saturated ethereal hydrogen chloride. An additional 150 ml of plain ether was added to maximize crystallization of the product. This was collected, washed with ether, and dried to afford 5.0 g (57%) of salt. Recrystallization from methanol-ether furnished 4.1 g (47%) of trans-1-(4-Chloro-2-fluorobenzyl)-2-(dimethylaminomethyl)cyclohexan-1-ol Hydrochloride, m.p. 185°–188°.

ANALYSIS

Calculated for $C_{16}H_{23}ClFNO.HCl$: 57.15%C, 7.19%H, 4.16%N,
Found: 57.28%C, 7.10%H, 4.06%N.

EXAMPLE 6 cis-1-(2-Fluorobenzyl)-2-(diethylaminomethyl)cyclohexan-1-ol Hydrochloride

To a stirred mixture, under $N_2$, of 16.0 g of magnesium turnings in 150 ml of anhydrous ether was added dropwise a solution of 86.2 g of 2-fluorobenzyl chloride in 150 ml ether. When the first few mls were charged, reaction began to take place, exothermically bringing the ether to reflux. This was cooled slightly and the temperature was maintained at about 30° by the rate of addition (0.5 hours). After the Grignard-forming reaction was complete, the mixture was aged for 0.5 hours and then cooled and kept at 15°–20° during the slow addition (1 hr.) of a solution of 110.0 g of 2-diethylaminomethylcyclohexanone in 125 ml. ether. After stirring 1 hour at room temperature the mixture was cooled to approximately 10° and quenched by the cautious addition of saturated ammonium chloride solution. The ether layer was decanted from the resulting gelatinous material. The gelatinous material was washed twice with ether. The combined ether layers were washed again with saturated ammonium chloride solution followed by a washing with brine, dried over $Na_2SO_4$, and concentrated in vacuo to an oil weighing 131.7 g (94% yield). From TLC analysis this oil was shown to be a mixture of cis and trans alcohols. The mixture was separated via formation of the hydrochloride salt. To this end, the oil was dissolved in 200 ml ethanol and cooled in an ice bath with stirring during the dropwise addition of 100 ml of a solution of ether saturated with hydrogen chloride. After the addition of 600 ml anhydrous ether and stirring for 3 hours the crystals were collected and washed with 200 ml of 3:1 ether/ethanol solution and finally with 800 ml ether, and dried to afford 60.6 g (38% yield) of a purified cis alcohol hydrochloride salt. Final purification was accomplished by recrystallizing 10 g of the above salt from 100 ml of 1:1 ethanol/ether, which afforded 8.25 g (31% overall yield) of cis-1-(2-Fluorobenzyl)-2-(diethylaminomethyl)cyclohexan-1-ol Hydrochloride m.p. 193°–194° C.

ANALYSIS

Calculated for $C_{18}H_{28}FNO.HCl$: 65.54%C, 8.86%H, 4.25%N,
Found: 65.45%C, 8.79%H, 3.99%N.

(b)
trans-1-(2-Fluorobenzyl)-2-(diethylaminomethyl)cyclohexan-1-ol Hydrochloride As indicated in Example 6(a), the cis isomer was separated from the trans isomer by formation of the hydrochloride salt. The mother liquor from this salt formation, now rich in the trans alcohol, was concentrated and the residue was reversed back to the free base. This material was purified further by high pressure liquid chromatography (HPLC) using an eluant of 6:1 toluene:methanol. Concentration in vacuo gave 17.0 g of the trans isomer as an oil. The oil was converted to the hydrochloride salt by dissolving 5.0 g of the above oil in 75 ml of a 2:1 ether/ethanol solution. To this ice cold solution was added 8 ml of anhydrous ether saturated with hydrogen chloride followed by an additional portion of ether. The mixture was stirred for 15 minutes and the solid collected to give 3.3 g of the hydrochloride salt. The resultant product was recrystallized from a 4:1 ether/ethanol solution to give 2.8 g of trans-1-(2-Fluorobenzyl)-2-(diethylaminomethyl)cyclohexan-1-ol Hydrochloride m.p. 186°–188° C.

ANALYSIS

Calculated for $C_{18}H_{28}FNO \cdot HCl$: 65.54%C, 8.86%H, 4.25%N,
Found: 65.48%C, 8.84%H, 4.01%N.

EXAMPLE 7

(a)

cis-1-(5-Chloro-2-fluorobenzyl)-2-(diethylaminomethyl)cyclohexan-1-ol Hydrochloride To a stirred mixture, under $N_2$, of 14.5 g of magnesium turnings and 250 ml of anhydrous ether was added dropwise a solution of 107.4 g of 5-chloro-2-fluorobenzyl chloride in 250 ml of ether. After an initial charge of 25 ml, reaction began to take place within 10–15 minutes, spontaneously bringing the ether to reflux. The rate of addition and occasion cooling maintained the reaction temperature at 25°–30° during the 0.75 hour addition period. The mixture containing the Grignard reagent was stirred at room temperature for 0.5 hours, then cooled and kept between 15°–20° during the addition over 1.0 hour of a solution of 91.7 g of 2-diethylaminomethylcyclohexanone in 250 ml of ether. After the addition was complete, the reaction mixture was stirred at room temperature for 1.0 hours and then cooled and kept at 0°–10° while being quenched by addition of 250 ml of saturated ammonium chloride solution. The gelatinous mixture was filtered through a pad of celite to give two clear layers. The aqueous layer was extracted twice with 250 ml of ether. The combined ether layers were washed twice with dilute brine, dried over sodium sulfate and concentrated in vacuo to an oil weighing 138 g (84%). An estimation from TLC indicated this consisted of an 85:15 cis:trans ratio of alcohols. This mixture was separated via the hydrochloride salt in the following manner. The above oil was dissolved in 250 ml of isopropanol, cooled to 0°, and then with good stirring, 250 ml of saturated ethereal hydrogen chloride was added dropwise over 45 minutes. Then 500 ml of plain ether was added slowly to maximize precipitation of product salt. The solid was collected, washed well with ether and dried. Recrystallization twice from ethanol provided 28.3 g (16% overall yield) of cis-1-(5-Chloro-2-fluorobenzyl)-2-(diethylaminomethyl)-cyclohexan-1-ol Hydrochloride m.p. 183°–186°.

ANALYSIS

Calculated for $C_{18}H_{27}ClFNO \cdot HCl$: 59.34%C, 7.75%H, 3.84%N,
Found: 59.24%C, 7.83%H, 3.80%N.

(b)

trans-1-(5-Chloro-2-fluorobenzyl)-2-(diethylaminomethyl)cyclohexan-1-ol Oxalate

As indicated in Example 7(a), the cis isomer was separated from the trans isomer by formation of the hydrochloride salt. The mother liquor from the salt formation, now rich in the trans alcohol, was concentrated in vacuo and the residue was reversed back to the free base. This material (78 g) was taken up in 100 ml of hexane, filtered, and the solution was adsorbed on a column containing 1.5 kg of silica gel packed in hexane. Elution first with hexane, then with toluene, followed by increasing percentages (10% per step) of chloroform in toluene, and finally with increasing percentages (1% per step) of methanol in chloroform brought forth the pure trans isomer with 2–3% methanol in chloroform. After combining and concentrating the desired fractions, 24.8 g (15.1% overall yield from the Grignard reaction) of the trans alcohol was obtained. 4.92 g of this product was converted to the oxalate salt in the following manner. The 4.92 g was taken up in 10 ml of ethanol, filtered, and treated with a solution of 1.35 g of oxalic acid in 20 ml of ethanol. After 20 ml of ether was added, scratching induced crystallization. The product salt was collected to afford 3.8 g (9.2% overall yield from the Grignard reaction), with m.p. 160°–162°. Recrystallization from ethanol-ether yielded trans-1-(5-Chloro-2-fluorobenzyl)-2-(diethylaminomethyl)-cyclohexan-1-ol Oxalate m.p. 160°–162°.

ANALYSIS

Calculated for $C_{16}H_{27}ClFNO \cdot C_2H_2O_4$: 57.48%C, 6.99%H, 3.35%N,
Found: 57.38%C, 6.91%H, 3.21%N.

EXAMPLE 8

(a)

cis-1-(2-Fluorobenzyl)-2-(di-n-propylaminomethyl)cyclohexan-1-ol Hydrochloride

To a stirred mixture, under $N_2$, of 12.6 g of magnesium turnings in 150 ml of anhydrous ether was added dropwise a solution of 67.5 g of 2-fluorobenzyl chloride in 150 ml ether. When the first few mls. were charged, reaction began to take place, exothermically bringing the ether to reflux. This was cooled slightly and the temperature was maintained at about 30° by the rate of addition (0.5 hr). After the Grignard-forming reaction was complete, the mixture was aged for 0.5 hours and then cooled and kept at 15°–20° during the slow addition (1 hour) of a solution of 116.5 g of 2-di-n-propylaminomethylcyclohexanone in 125 ml ether. After stirring 1 hour at room temperature the mixture was cooled to approximately 10° and quenched by the cautious addition of 150 ml of saturated ammonium chloride solution. The ether layer was decanted from the resulting gelatinous material. The gelatinous material was washed twice with an additional 150 ml of ether. The combined ether layers were washed again with saturated ammonium chloride solution followed by a washing with saturated brine, dried over $Na_2SO_4$, and concentrated in vacuo to an oil weighing 129.39 g (100% yield). From TLC analysis this oil was shown to be a mixture of cis and trans alcohols. The mixture was separated by dissolving the oil in 200 ml of ethanol and cooling on an ice bath with stirring during the dropwise addition of 100 ml of a solution of ether saturated with hydrogen chloride. After the addition of 600 ml anhydrous ether and stirring for 3 hours the crystals were collected and washed with 400 ml of an ice cold 3:1 ether/ethanol solution and finally with 800 ml of ether, and dried to afford 80.08 g (57% yield) of a purified cis alcohol hydrochloride salt, m.p. 201°–203°. Recrystallization of 10 g of the above salt from 100 ml of 1:1 ethanol/ether afforded 7.0 g of cis-1-(2-Fluorobenzyl)-2-(di-n-propylaminomethyl)cyclohexan-1-ol Hydrochloride, melting point unchanged.

ANALYSIS

Calculated for $C_{20}H_{32}FNO \cdot HCl$: 67.11%C, 9.29%H, 3.91%N,

Found: 66.96%C, 9.13%H, 3.55%N.

(b) trans-1-(2-Fluorobenzyl)-2-(di-n-propylaminomethyl)-cyclohexan-1-ol Hydrochloride As indicated in Example 8(a), the cis isomer was separated from the trans isomer by formation of the hydrochloride salt. The mother liquor from the salt formation, now rich in the trans alcohol, was concentrated and the residue reversed back to the free base. This material (52.8 g) was dissolved in 350 ml of a 6:1 ether-ethanol solution and cooled in an ice bath. To this was added dropwise 50 ml of a solution of ether saturated with hydrogen chloride, followed by an additional 100 ml of ether. This gave 14.0 g of the crude trans alcohol as the hydrochloride salt. Recrystallization from 280 ml of a 2.5:1 ether-ethanol solution afforded 9.1 g (6.5% yield) of trans-1-(2-Fluorobenzyl)-2-(di-n-propylaminomethyl)-cyclohexan-1-ol Hydrochloride, m.p. 185°–187° C.

ANALYSIS

Calculated for $C_{20}H_{32}FNO \cdot HCl$: 67.11%C, 9.29%H, 3.91%N,

Found: 66.99%C, 9.24%H, 3.64%N.

EXAMPLE 9

(a) cis-1-(5-Chloro-2-fluorobenzyl)-2-(di-n-propylaminomethyl)cyclohexan-1-ol Hydrochloride To a stirred mixture, under $N_2$, of 11.2 g of magnesium turnings and 250 ml of anhydrous ether was added dropwise a solution of 32.3 g of 5-chloro-2-fluorobenzyl chloride in 250 ml of ether. After an initial charge of 25 ml, reaction began to take place, spontaneously bringing the ether to reflux. The rate of addition and occasional cooling maintained the reaction temperature at about 30° during the 1.0 hour addition period. The mixture containing the Grignard reagent was stirred at room temperature for 0.5 hr. and then cooled and kept between 15°–20° during the addition over 1.0 hours of a solution of 81.2 g of 2-di-n-propylaminomethylcyclohexanone in 250 ml of ether. After an additional 1 hour at room temperature, the reaction was cooled and kept at 0°–10° while being quenched by addition of 250 ml of saturated ammonium chloride solution. The mixture was filtered through a pad of celite, and the layers were separated. The aqueous phase was extracted once with 250 ml of ether. The combined ether layers were washed once with ammonium chloride solution, twice with dilute brine, dried over anhydrous sodium sulfate, and concentrated in vacuo to an oil weighing 131 g (97%). An estimation from TLC indicated this consisted of a 85:15 ratio of cis:trans alcohol. This mixture was separated by dissolving the oil in 250 ml 2-propanol, and with good stirring and cooling, was treated dropwise over 45 minutes with 250 ml of ether saturated with HCl. An additional 750 ml of ether was added before the product salt was filtered, washed with 1:4 2-propanol:ether, thrice with ether and dried to afford 54 g (36% overall yield) of the salt, m.p. 171°–175°. A sample of cis-1-(5-Chloro-2-fluorobenzyl)-2-(di-n-propylaminomethyl)cyclohexan-1-ol Hydrochloride was recrystallized from ethanol-ether and had an m.p. 172°–175°.

ANALYSIS

Calculated for $C_{20}H_{31}ClFNO \cdot HCl$: 61.22%C, 8.22%H, 3.57%N,

Found: 61.58%C, 8.18%H, 3.39%N.

EXAMPLE 10

(1'β,2'β)-2'-Dimethylaminomethylspiro[benzofuran-2(3H),1'-cyclohexane] Hydrochloride A stirred mixture, under $N_2$, of 10.6 g cis-2-(dimethylaminomethyl)-1-(2-fluorobenzyl)-cyclohexan-1-ol and 2.4 g of 50% sodium hydride in an oil dispersion in 60 ml of benzene and 20 ml dimethylformamide was refluxed for 3 hours. The mixture was then carefully decanted into 600 ml of ice water, with good stirring. After 10 minutes, 300 ml of $CH_2Cl_2$ was added and stirring was continued for 10 minutes more. The organic phase was separated, washed once with dilute brine, dried over $Na_2SO_4$ and concentrated to an oil. This was dissolved in 40 ml of ethanol and the solution treated with ethereal hydrogen chloride to the turbidity point. After stirring for 1 hour the solid was collected (6.20 g) and recrystallized from ethanol-ether to afford (1'β,2'β)-2'-Dimethylaminomethylspiro[benzofuran-2(3H),1'-cyclohexane]hydrochloride, m.p. 260°–262°.

ANALYSIS

Calculated for $C_{16}H_{23}NO \cdot HCl$: 68.19%C, 8.58%H, 4.97%N,

Found: 68.18%C, 8.29%H, 4.79%N.

EXAMPLE 11

(1'β,2'β)-2'-Dimethylaminomethylspiro[5-chlorobenzofuran-2-(3H),1'-cyclohexane] Hydrochloride A stirred mixture, under $N_2$, of 10.2 g cis-1-(5-chloro-2-fluorobenzyl)-2-(dimethylaminomethyl)-cyclohexan-1-ol, 2.00 g of 61% sodium hydride in an oil dispersion and 200 ml of benzene was heated close to the boiling point. Then 50 ml of dry dimethylformamide was added and the mixture was refluxed for 3 hours. After cooling, the reaction fluid was decanted cautiously into 2 liters of ice and water with good stirring. Then 250 ml of dichloromethane was added to extract the product. The aqueous phase was separated and extracted twice more with $CH_2Cl_2$. The organic phases were combined, washed twice with dilute brine, dried over sodium sulfate and concentrated in vacuo to 7.70 g of an oil. The oil was dissolved in 35 ml of hot ethanol and treated with 50 ml of ethereal hydrogen chloride, followed by 25 ml of ether in small portions, with stirring. The resultant precipitated HCl salt was collected to afford 4.2 g (39% overall yield), m.p. 245°–250°. Recrystallization from ethanol (charcoal)-ether gave 3.35 g (31% yield) of (1'β,2'β)-2'-Dimethylaminomethylspiro[5-chlorobenzofuran-2(3H,1'-cyclohexane] Hydrochloride, m.p. 259°–261°.

ANALYSIS

Calculated for $C_{16}H_{22}ClNO \cdot HCl$: 60.76%C, 7.33%H, 4.43%N,

Found: 60.58%C, 7.45%H, 4.54%N.

EXAMPLE 12

(1'β,2'β)-2'-Dimethylaminomethylspiro[4-chlorobenzofuran-2-(3H),1'-cyclohexane] Hydrochloride A stirred mixture, under $N_2$, of 27.0 g of cis-1-(2-chloro-6-fluorobenzyl)-2-(dimethylaminomethyl)-cyclohexan-1-ol, 5.25 g of 61% sodium hydride in an oil dispersion, 600 ml of benzene and 150 ml of dimethylformamide was refluxed for 1.5 hours. After cooling, the reaction mixture was cautiously decanted into 500 ml of ice and water, with good stirring. Then 250 ml of ether was added to extract the product. The aqueous phase was separated and extracted twice more with 250 ml of ether. The ether phases were combined, washed twice with brine, dried over $Na_2SO_4$ and concentrated in vacuo to 25.4 g (100%) of oil. This was dissolved in 50 ml of ethanol, cooled to 0°, and then, with good stirring, 100 ml of ether saturated with hydrogen chloride was added. An additional 500 ml of ether was then added to maximize precipitation. The HCl salt was collected to afford 21.7 g (76%), m.p. 245°–248°. Recrystallization from ethanol-ether afforded 9.0 g of pure crystals, m.p. 249°–251°.

ANALYSIS

Calculated for $C_{16}H_{22}ClNO.HCl$: 60.76%C, 7.33%H, 4.43%N,
Found: 60.67%C, 7.52%H, 4.38%N.

EXAMPLE 13

(1'β,2'β)-2'-Dimethylaminomethylspiro[6-chlorobenzofuran-2-(3H),1'-cyclohexane] Hydrochloride A stirred mixture, under $N_2$, of 21.0 g of cis-1-(4-chloro-2-fluorobenzyl)-2-(dimethylaminomethyl)-cyclohexan-1-ol, 4.13 g of 61% sodium hydride in an oil dispersion, 500 ml of dry benzene and 125 ml of dry dimethylformamide was heated at reflux for 1.0 hour. After cooling, the reaction fluid was decanted cautiously into 500 ml of ice and water, with good stirring. After all of the excess NaH had been destroyed, 500 ml of ether was added to extract the product. The aqueous phase was separated and reextracted twice more with 250 ml of ether. The organic phases were combined, washed twice with brine, dried over sodium sulfate and concentrated in vacuo to an oil weighing 19.4 g (100%).

The oil was dissolved in 50 ml of ethanol, and the solution was stirred and cooled in an ice bath. Then 100 ml of saturated ethereal hydrogen chloride was added in several portions. An additional 500 ml of ether was added in portions to maximize precipitation of the product hydrochloride salt. This was collected, washed well with ether, and dried to afford 17.5 g (79% overall yield), m.p. 257°–259°, of TLC pure salt. This was recrystallized from ethanol-ether to furnish 14.7 g (67% overall yield) of (1'β,2'β)-2'-Dimethylaminomethylspiro-[6-chlorobenzofuran-2(3H),1'-cyclohexane] hydrochloride, m.p. 258°–259°.

ANALYSIS

Calculated for $C_{16}H_{22}ClNO.HCl$: 60.76%C, 7.33%H, 4.43%N,
Found: 60.67%C, 7.23%H, 4.41%N.

EXAMPLE 14

(1'β,2'β)-2'-Diethylaminomethylspiro[benzofuran-2(3H),1'-cyclohexane] Hydrochloride A stirred mixture of $N_2$, of 19.0 g of cis-1-(2-Fluorobenzyl)-2-(diethylaminomethyl)cyclohexan-1-ol, and 5.0 g of 61% sodium hydride in an oil dispersion in 300 ml of benzene and 75 ml dimethylformamide was refluxed for 4 hours. After 2 hours of refluxing an additional 4.0 g of NaH was added to achieve complete cyclization of starting material. After cooling, the reaction mixture was cautiously decanted into 600 ml of ice and water, with good stirring. Then 600 ml of ether was added to extract the product. The aqueous phase was separated and extracted thrice with 200 ml ether. The combined ether phases were washed with saturated brine, dried over $Na_2SO_4$ and concentrated in vacuo to 17.2 g (97%) of an oil. This was dissolved in 50 ml of ethanol, cooled and then with good stirring 15 ml of ether saturated with hydrogen chloride was added dropwise. An additional 200 ml of anhydrous ether was then added to maximize precipitation. The hydrochloride salt was collected and washed well with ether to give 8.6 g (43%) of a solid m.p. 165°–173° C. Recrystallization from 50 ml of 1:1 ethanol/ether afforded 3.4 g (17% overall yield) of (1'β,2'β)-2'-Diethylaminomethylspiro[benzofuran-2(3H),1'-cyclohexane] Hydrochloride, m.p. 176°–178° C.

ANALYSIS

Calculated for $C_{18}H_{27}NO.HCl$: 69.77%C, 9.11%H, 4.52%N,
Found: 69.56%C, 9.08%H, 4.27%N.

EXAMPLE 15

(1'β,2'β)-2'-Diethylaminomethylspiro[5-chlorobenzofuran-2-(3H),1'-cyclohexane] Hydrochloride A stirred mixture under $N_2$ of 16.4 g cis-1-(5-chloro-2-fluorobenzyl)-2-(diethylaminomethyl)-cyclohexan-1-ol, 5.31 g of 61% sodium hydride in an oil dispersion, 400 ml of dry benzene and 100 ml of dry dimethylformamide was refluxed for 4 hours. After cooling, the reaction mixture was decanted cautiously into 500 ml of ice and water, with good stirring. Then 500 ml of ether was added to extract the product. The aqueous phase was separated and extracted again with 250 ml of ether. The organic phases were combined, washed twice with dilute brine, dried over sodium sulfate and concentrated in vacuo to 11.0 g (81%) of an oil. This was dissolved in 20 ml of absolute ethanol, cooled in ice with stirring, and treated dropwise with 30 ml of ethereal hydrogen chloride, followed by 70 ml of plain ether. The precipitate HCl salt was collected to afford 3.8 g (25% overall yield) m.p. 210°–218°. Recrystallization (charcoal) from ethanol-ether gave 1.60 g (10.3% overall yield) of (1'β,2'β)-2'-Diethylaminomethylspiro[5-chlorobenzofuran-2(3H),1'-cyclohexane] Hydrochloride m.p. 222°–225°.

ANALYSIS

Calculated for $C_{18}H_{26}ClNO.HCl$: 62.79%C, 7.90%H, 4.07%N,
Found: 62.64%C, 7.80%H, 3.80%N.

EXAMPLE 16

(1',2'β)-2'-Di-n-propylaminomethylspiro[benzofuran-2(3H),-1'-cyclohexane] Hydrochloride A well stirred mixture, under $N_2$, of 21.8 g cis-1-(2-fluorobenzyl)-2-(di-n-propylaminomethyl)cyclohexan-1-ol, 4.0 g of 61% sodium hydride in an oil dispersion, 300 ml benzene and 75 ml dimethylformamide (DMF) was refluxed for 4 hours. After cooling, the reaction mixture was poured into 600 ml of ice and water and stirred well. Then 600 ml of ether was added to extract the product. The aqueous layer was separated and washed thrice with 200 ml ether. The combined ether phases were washed with brine, dried over $Na_2SO_4$, and concentrated in vacuo, yielding 19.3 g (98% yield) of an oil.

Initial purification of this material was accomplished via formation of the oxalate salt. To this end, 16.0 g of the above oil was dissolved in 50 ml of ethanol and cooled in an ice bath. To this was added 5.0 g of oxalic acid in 40 ml of ethanol, followed by 100 ml of ether. After stirring 2 hours, 11.0 g of the oxalate salt was collected. The oxalate salt was reversed back to the free base by partitioning it between 100 ml $H_2O$ and 100 ml $CH_2Cl_2$. The ice cold mixture was made basic to litmus with 25% NaOH. The aqueous layer was separated and washed with 50 ml $CH_2Cl_2$. The combined organic phases were then washed with brine, dried over $Na_2SO_4$, and concentrated in vacuo to give 6.4 g of an oil. Final purification as the hydrochloride salt was accomplished by dissolving the above oil in 100 ml ether. This was cooled in an ice bath and then 5.0 ml of ether saturated with hydrogen chloride was added dropwise. Upon addition of more ether (200 ml) and scratching, 7.0 g of the solid hydrochloride salt was obtained. This solid was recrystallized from 410 ml of a 1:40 ethanol-ether solution yielding 3.0 g (14% overall yield) of (1'β,2'β)-2'-Di-n-propylaminomethylspiro[benzofuran-2(3H),1'-cyclohexane] Hydrochloride, m.p. 116°–119° C.

ANALYSIS

Calculated for $C_{20}H_{31}NO\cdot HCl$: 71.11%C, 9.55%H, 4.15%N,
Found: 70.47%C, 9.46%H, 4.09%N.

EXAMPLE 17

(1'β,2'β)-2'-Di-n-propylaminomethylspiro[5-chlorobenzofuran-2(3H),1'-cyclohexane] Fumarate A stirred mixture, under $N_2$, of 35.6 g of cis-1-(5-chloro-2-fluorobenzyl)-2-(di-n-propylaminomethyl)-cyclohexan-1-ol, 7.87 g of 61% sodium hydride in an oil dispersion, 700 ml of benzene and 150 ml of dimethylformamide was refluxed for 2 hours. After cooling, the reaction mixture was cautiously decanted into 500 ml of ice and water, with good stirring. Then 500 ml of ether was added to extract the product. The aqueous phase was separated and extracted once more with 250 ml of ether. The ether phases were combined, washed twice with dilute brine, dried over $Na_2SO_4$, and concentrated in vacuo to 24.6 g (73%) of oil. A portion of this oil (9.0 g) was dissolved in 20 ml of ethanol and treated with a hot solution of 3.13 g of fumaric acid in 30 ml of ethanol. The solution was concentrated to 25 ml of ethanol and the product fumarate salt was allowed to crystallize. This afforded 2.0 g (16.4% overall yield) of salt. Recrystallization from ethanol furnished 1.4 g (8.4% overall yield) of (1'β,2'β)-2'-Di-n-propylaminomethyl-spiro[5-chlorobenzofuran-2(3H),1'-cyclohexane] Fumarate, m.p. 163°–167°.

ANALYSIS

Calculated for $C_{20}H_{30}ClNO\cdot C_4H_4O_4$: 63.78%C, 7.58%H, 3.10%N,
Found: 63.85%C, 7.70%H, 3.02%N,

EXAMPLE 18

(1'β2'β)-2'-Dimethylaminomethylspiro[5-fluorobenzofuran-2(3H),-1'-cyclohexane] Hydrochloride To a stirred solution, under $N_2$, of 11.3 g cis-1-(2,5-difluorobenzyl)-2-(dimethylaminomethyl)cyclohexan-1-ol in 500 ml of anhydrous benzene was added 30 ml of a 2 molar solution of phenyl lithium in 70% benzene/30% ether, in one portion. The reaction was heated at reflux for 1.0 hour, then cooled and quenched by addition of 400 ml of dilute brine. The resulting emulsion was broken by filtration and the layers were separated. The organic phase was extracted once with dilute brine, dried over $Na_2SO_4$, and concentrated in vacuo to an oil weighing 11.2 g. This was dissolved in 20 ml of ethanol and treated with 100 ml of ethereal hydrogen chloride. An additional 100 ml of fresh ether was added to complete the precipitation of the hydrochloride salt, 8.5 g (71% overall yield) of (1'β,2'β)-2'-Dimethylaminomethyl-spiro[5-fluorobenzofuran-2(3H),1'-cyclohexane] Hydrochloride, m.p. 248°–251° dec.

ANALYSIS

Calculated for $C_{16}H_{22}FNO\cdot HCl$: 64.10%C, 7.73%H, 4.67%N,
Found: 63.87%C, 7.71%H, 4.56%N.

EXAMPLE 19

(1'α,2'β)-2'-Dimethylaminomethylspiro[benzofuran-2(3H),1'-cyclohexane] Hydrochloride A stirred mixture, under $N_2$, of 8.00 g of trans-2-(dimethylaminomethyl)-1-(2-fluorobenzyl)-cyclohexan-1-ol, 1.77 g of 61% sodium hydride in an oil dispersion and 80 ml of dry toluene was heated close to boiling. Then 80 ml of dry dimethylformamide was added and the mixture was refluxed for 2.0 hours. After cooling, the reaction fluid was decanted cautiously into 2 l of ice and water, with good stirring. Then 500 ml of ether was added to extract the product. The aqueous phase was separated and extracted twice more with 500 ml of ether. The ether phases were combined, washed twice with dilute brine, dried over sodium sulfate, and concentrated in vacuo to 7.9 g of oil. This was dissolved in 20 ml of ethanol and treated with 100 ml of ethereal hydrogen chloride followed by 50 ml of ether. The precipitated HCl salt was collected to give 3.2 g (38% overall yield), m.p. 210°–218° C. Recrystallization from ethanol (charcoal)-ether gave 1.5 g (18% yield) of (1'α,2'β)-2'-Dimethylaminomethylspiro[benzofuran-2(3H),1'-cyclohexane] Hydrochloride, m.p. 215°–218°.

ANALYSIS

Calculated for $C_{16}H_{23}NO\cdot HCl$: 68.19%C, 8.58%H, 4.97%N,
Found: 68.21%C, 8.40%H, 4.93%N.

EXAMPLE 20

(1'α,2'β)-2'-Dimethylaminomethylspiro[5-chlorobenzofuran-2(3H),1'-cyclohexane] Hydrochloride A stirred mixture, under $N_2$ of 12.0 g of trans-1-(5-chloro-2-fluorobenzyl)-2-(dimethylaminomethyl)-cyclohexan-1-ol, 2.40 g of 61% sodium hydride in an oil dispersion, 300 ml of benzene and 75 ml of dimethylformamide was heated at reflux for 2 hours. After cooling, the reaction fluid was decanted cautiously into 500 ml of ice and water, with good stirring. Then 250 ml of ether was added to extract the product. The aqueous phase was separated and re-extracted twice more with 250 ml of ether. The organic phases were combined, washed twice with brine, dried over sodium sulfate and concentrated in vacuo to an oil weighing 10.2 g (91%).

This oil was dissolved in 150 ml of ether and treated with 50 ml of ethereal hydrogen chloride dropwise over a 20 minute period, with good stirring. The hydrochloride salt separated out as a solid. This was filtered, washed repeatedly with ether and then dissolved in 15 ml of hot ethanol to which 150 ml of ether was added. This afforded 7.1 g (56% overall yield) of salt m.p. 177°–194°. Recrystallization first from ethanol-ether (yielding 3.5 g, m.p. 187°–194°) and then from acetone furnished 2.4 g (19% overall yield) of (1'α,2'β)-2'-Dimethylaminomethylspiro[5-chlorobenzofuran-2(3H),1'-cyclohexane] Hydrochloride, m.p. 199°–202°.

ANALYSIS

Calculated for $C_{16}H_{22}ClNO \cdot HCl$: 60.76%C, 7.33%H, 4.43%N,

Found: 60.61%C, 7.26%H, 4.38%N.

EXAMPLE 21

(1'α2'β)-2'-Dimethylaminomethylspiro[4-chlorobenzofuran-2-(3H),1'-cyclohexane] Hydrochloride A stirred mixture, under $N_2$, of 7.5 g of trans-1-(2-fluoro-6-chlorobenzyl)-2-(dimethylaminomethyl)-cyclohexan-1-ol, 1.18 g of 6% sodium hydride in an oil dispersion, 150 ml benzene and 40 ml dimethylformamide was refluxed for 4 hours. After cooling, the reaction mixture was cautiously poured into 500 ml of ice and water, with good stirring. Then 400 ml of ether was added to extract the product. The aqueous phase was separated and extracted thrice with 150 ml of ether. The combined ether phases were washed with brine, dried over $Na_2SO_4$ and concentrated in vacuo to 6.4 g (91% yield) of an oil. This oil was purified by dissolving it in 40 ml of absolute ethanol and subsequently cooling on ice. To this was added dropwise 15 ml of ether saturated with hydrogen chloride. An additional 150 ml of anhydrous ether was added to maximize precipitation. The hydrochloride salt was collected to afford 4.2 g (53% yield), m.p. 228°–230°. Recrystallization from a 5:1 ether/ethanol solution gave 2.7 g (34% overall yield) of (1'α2'β)-2'-Dimethylaminomethylspiro[4-chlorobenzofuran-2(3H),1'-cyclohexane] Hydrochloride, m.p. 231°–233° C.

ANALYSIS

Calculated for $C_{16}H_{22}ClNO \cdot HCl$: 60.76%C, 7.33%H, 4.43%N,

Found: 60.62%C, 7.33%H, 4.34%N.

EXAMPLE 22

(1'α,2'β)-2'-Dimethylaminomethylspiro[6-chlorobenzofuran-2(3H),-1'-cyclohexane] Hydrochloride A stirred mixture, under $N_2$, of 13.5 g of trans-1-(4-chloro-2-fluorobenzyl)-2-(dimethylaminomethyl)cyclohexan-1-ol, 2.67 g of 61% sodium hydride in an oil dispersion, 300 ml of benzene and 75 ml of dimethylformamide was refluxed for 1.0 hour. After cooling, the reaction mixture was cautiously decanted into 500 ml of ice and water, with good stirring. Then 250 ml of ether was added to extract the product. The aqueous phase was separated and extracted once more with 250 ml of ether. The ether phases were combined, washed twice with dilute brine, dried over $Na_2SO_4$, and concentrated in vacuo to 13.0 g of oil. This was dissolved in 50 ml of ethanol, cooled to 0°, and then, with good stirring, 100 ml of ether saturated with hydrogen chloride was added in portions. An additional 200 ml of ether was added to maximize precipitation. The HCl salt was collected to afford 9.3 g (65% overall yield, m.p. 254°–255° C. Ethanol-ether afforded 6.3 g (44% overall yield) of (1'α,1'β)-2'-Dimethylaminomethylspiro[6-chlorobenzofuran-2(3H),1'-cyclohexane] Hydrochloride, m.p. 255°–256° C.

ANALYSIS

Calculated for $C_{16}H_{22}ClNO \cdot HCl$: 60.76%C, 7.33%H, 4.43%N,

Found: 60.61%C, 7.26%H, 4.37%N.

EXAMPLE 23

(1'α,2'β)-2'-Diethylaminomethylspiro[benzofuran-2(3H),1'-cyclohexane] Hydrobromide A stirred mixture, under $N_2$, of 12.0 g of trans-1-(2-fluorobenzyl)-2-(diethylaminomethyl)cyclohexan-1-ol, 3.2 g of 61% sodium hydride in an oil dispersion, in 250 ml of benzene and 60 ml dimethylformamide was refluxed for 4 hours. After 2½ hours of refluxing, an additional 2.0 g of the 61% NaH was added to assure complete cyclization of the starting material. After cooling, the reaction mixture was cautiously poured into 500 ml of ice and water with good stirring. Then 500 ml of ether was added to extract the product. The aqueous phase was separated and extracted twice with 150 ml of ether. The combined ether phases were washed with brine, dried over $Na_2SO_4$ and concentrated in vacuo to 11.4 g (100% yield) of an oil. This oil was initially purified by column chromatography using 100 g of silica gel and a 9:1 toluene/methanol solution as an eluant. Two grams of the purified oil was converted to the hydrobromide salt by dissolving it in 10 ml n-butanol and cooling in an ice bath, with subsequent dropwise addition of freshly prepared ether saturated with hydrogen bromide. Addition of isopropyl ether (over 100 ml) and seeding produced 1.0 g of pure (1'α,2'β)-2'-Diethylaminomethylspiro[benzofuran-2(3H),1'-cyclohexane] Hydrobromide, m.p., 143°–145° C.

ANALYSIS

Calculated for $C_{18}H_{27}NO \cdot HBr$: 61.02%C, 7.97%H, 3.95%N,

Found: 61.07%C, 7.79%H, 3.86%N.

EXAMPLE 24

(1′β,2′β)-2′-Dimethylaminomethylspiro[5-bromobenzofuran-2(3H),1′-cyclohexane] Hydrochloride To a stirred solution at room temperature of 10.0 g of (1′β,2′β)-dimethylaminomethylspiro[benzofuran-2(3H),1′-cyclohexane] hydrochloride in 250 ml of methanol was added 6.3 g of N-bromosuccinimide (N.B.S.). Addition of the N.B.S. produced a light yellow solution along with a 7° rise in temperature. The solution was stirred for ½ hr. at room temperature at which time thin layer chromatography (TLC) indicated the reaction to be complete. The solution was concentrated in vacuo to a solid, which was partitioned between 400 ml $CHCl_3$ and 400 ml $H_2O$. The aqueous phase was made basic by the addition of saturated $NaHCO_3$. After extraction, the separated aqueous phase was washed with an additional 100 ml of $CHCl_3$. The combined organic layers were then washed with brine and dried over $MgSO_4$. Concentration in vacuo gave 10.79 (95% yield) of product, m.p. 80°–82° C. This material was further purified by formation of the hydrochloride salt. To this end, the above solid was dissolved in 300 ml of absolute ethanol and cooled in ice. To this cooled solution was added dropwise 25 ml of ether saturated with hydrogen chloride. Seeding along with the addition of 200 ml of ether produced 10.8 g (86% yield) of the hydrochloride salt, m.p. 262°–264°. Recrystallization of the hydrochloride salt from ethanol-ether gave 8.7 g (69% yield) of (1′β,2′β)-2-dimethylaminomethylspiro[5-bromobenzofuran-2(3H),1′-cyclohexane] hydrochloride, m.p. 263°–265° C.

ANALYSIS

Calculated for $C_{16}H_{22}BrNO.HCl$: 53.28%C, 6.43%H, 3.88%N,
Found: 53.10%C, 6.37%H, 3.86%N.

EXAMPLE 25

(1′β,2′β)-2′-Dimethylaminomethylspiro[5,7-dibromobenzofuran-2(3H),1′-cyclohexane] Hydrochloride To a stirred solution of 5.0 g of (1′β, 2′β)-2′-dimethylaminomethylspiro[benzofuran-2(3H),1′-cyclohexane] hydrochloride in 100 ml of methanol was added 3.2 g of N.B.S. This was stirred for ½ hour and then brought to reflux at which time 3.2 g of N.B.S. and 2.3 g of N-chlorosuccinimide (N.C.S.) were added simultaneously. This solution was refluxed approximately 10 minutes and then cooled and concentrated in vacuo to a residue. The residue was taken up in 200 ml of $CH_2Cl_2$ and 200 ml $H_2O$ and the mixture was made basic with 2.5M NaOH. The separated aqueous phase was washed with 100 ml of $CH_2Cl_2$ and the combined organic phases were washed with brine and dried over $Na_2SO_4$. Concentration in vacuo gave 6.8 g (95% yield) of an oil. Purification via the hydrochloride salt was conducted by dissolving the oil in a mixture of 15 ml of absolute ethanol and 50 ml of anhydrous ether. The cooled solution was made acidic with the dropwise addition of ether saturated with hydrogen chloride. Addition of 200 ml of ether and cooling produced 3.0 g (39% yield) of crude hydrochloride salt. The crude salt was recrystallized twice from an ethyl acetate/methanol solution to give 2.1 g (27% yield) of (1′β,2′β)-2′-dimethylaminomethylspiro[5,7-dibromobenzofuran-2(3H),1′-cyclohexane] hydrochloride, m.p., 239°–240° C.

ANALYSIS

Calculated for $C_{16}H_{21}Br_2NO.HCl$: 43.71%C, 5.04%H, 3.19%N,
Found: 43.85%C, 5.00%H, 3.15%N.

EXAMPLE 26

(1′β,2′β)-2′-Dimethylaminomethylspiro[5-methylbenzofuran-2(3H),1′-cyclohexane] Hydrochloride To a stirred solution, under $N_2$, of 13 ml of 2.2M n-butyllithium in hexane and 50 ml of dry tetrahydrofuran at −60° was added dropwise a solution of 7.8 g of (1′β,2′β)-2′-dimethylaminomethylspiro[5-bromobenzofuran-2(3H),1′-cyclohexane] in 100 ml dry THF. After complete addition, the solution was stirred at −60° for 1.5 hours. The intermediate was transferred via a double tipped needle to a solution, under $N_2$, of 2.6 ml of dimethylsulfate in 100 ml of THF at room temperature. This solution was stirred 1.5 hours and then quenched with 25 ml of 2.5M NaOH. The reaction mixture was concentrated in vacuo to a viscous liquid which was extracted with 100 ml of 2.5M NaOH and 300 ml ether. The separated aqueous phase was washed twice with 100 ml of ether. The combined ether phases were washed with brine, dried over $Na_2SO_4$ and concentrated in vacuo to give 4.84 g (78% yield) of an oil. Purification of the residue was afforded via the hydrochloride salt, which was obtained by dissolving the above oil in a mixture of absolute ethanol and 50 ml of anhydrous ether. The solution was cooled in an ice bath and acidified with a solution of ether saturated with hydrogen chloride. Further addition of 50 ml of ether with stirring, provided 4.8 g (68% yield) of hydrochloride salt, m.p., 262°–264° C. This solid was recrystallized twice, once from ethyl acetate/methanol and again from absolute ethanol to give 2.4 g (34% yield) of (1′β,2′β)-2′-dimethylaminomethylspiro[5-methylbenzofuran-2(3H),1′-cyclohexane] Hydrochloride, m.p. 266°–267° C.

ANALYSIS

Calculated for $C_{17}H_{25}NO.HCl$: 69.02%C, 8.86%H, 4.73%N, Found: 68.76%C, 8.89%H, 4.66%N.

EXAMPLE 27

(1′β,2′β)-2′-Dimethylaminomethylspiro[5-methoxybenzofuran-2-(3H),1′-cyclohexane] Hydrochloride To a stirred solution, under $N_2$, of 40.6 g of $NaOCH_3$ in 250 ml of anhydrous methanol was added 24.4 g of (1′β,2′β)-2′-dimethylaminomethylspiro[5-bromobenzofuran-2(3H),1′-cyclohexane] along with 350 ml of dry DMF and 28.6 g of CuI. This mixture was refluxed for 41 hours at which time it was cooled and filtered through celite. The filtrate was concentrated in vacuo to a solid, which was extracted with 500 ml of $CH_2Cl_2$ and 400 ml of $H_2O$. The separated aqueous phase was washed with an additional 100 ml of $CH_2Cl_2$ and the combined organic layers were washed with brine and dried over $Na_2SO_4$. This solution was concentrated in vacuo to give 14.95 g (72% yield) of an oil.

Further purification was achieved by formation of the hydrochloride salt. To this end, the above oil was dissolved in 50 ml. of absolute ethanol and 100 ml of anhydrous ether. The cooled solution was acidified with a solution of ether saturated with hydrogen chloride. The resulting solid was filtered and dried to provide 15.0 g (64% yield) of a solid. 10.0 g of this crude salt was recrystallized twice from absolute ethanol to give 3.8 g (24% yield) of (1'β,2'β)-2'-Dimethylaminomethylspiro[5-methoxybenzofuran-2(3H),1'-cyclohexane] hydrochloride, m.p.—247°–249° C.

ANALYSIS

Calculated for $C_{17}H_{25}NO_2 \cdot HCl$: 65.48%C, 8.40%H, 4.49%N, Found: 65.24%C, 8.38%H, 4.40%N.

EXAMPLE 28

(1'β,2'β)-2'-Dimethylaminomethylspiro[5,7-dichlorobenzofuran-2(3H),1'-cyclohexane] Hydrochloride To a stirred solution at room temperature of 5.0 g of (1'β,2'β)-2'-dimethylamino[benzofuran-2(3H),1'-cyclohexane] hydrochloride in 100 ml of methanol was added 2.4 g of N-chlorosuccinimide (N.C.S.). This solution was refluxed for 1 hour and then cooled to below 45° C., when a second portion (2.4 g) of N.C.S. was added. The solution was again refluxed for 1 hour and then cooled and concentrated in vacuo to remove the methanol. The resulting residue was partitioned between 100 ml of CHCl₃ and 100 ml of H₂O. The aqueous layer was made basic with saturated NaHCO₃, and after separation was washed with another 50 ml of CHCl₃. The combined organic layers were washed with brine, dried over MgSO₄, and concentrated in vacuo to 5.29 g (94% yield) of an oil.

This oil was further purified by formation of the hydrochloride salt. To this end, the above oil was dissolved in 25 ml of absolute ethanol and cooled in ice. To this was added dropwise a solution of ether saturated with hydrogen chloride until the ethanol solution became acidic. Seeding and the addition of 125 ml of ether produced 3.1 g (49% yield) of the crude hydrochloride salt, m.p. 232°–234° C. Recrystallization of this solid in a 3:1 ether/ethanol solution gave 2.4 g (38% yield) of (1'β,2'β)-2'-Dimethylaminomethylspiro[5,7-dichlorobenzofuran-2(3H),1'-cyclohexane] Hydrochloride, m.p. 233°–235° C.

ANALYSIS

Calculated for $C_{16}H_{21}Cl_2NO \cdot HCl$: 54.80%C, 6.32%H, 3.99%N, Found: 54.94%C, 6.42%H, 3.94%N.

EXAMPLE 29

(1'β,2'β)-2'-Dimethylaminomethylspiro[5,6,7-trichlorobenzofuran-2(3H),1'-cyclohexane] Hydrochloride A stirred solution, under N₂, of 2.53 g of (1'α,2'β)-2'-dimethylaminomethylspiro[6-chlorobenzofuran-2(3H),1'-cyclohexane] hydrochloride and 1.17 g of N-chlorosuccinimide (NCS) in 100 ml of methanol was refluxed for 2.0 hr. when 0.6 g more of NCS was added. An hour later, an additional charge of 0.6 g of NCS was added. One hour after the final portion of NCS was added, the solution was cooled and concentrated to a moist solid. This was partitioned between 100 ml of dichloromethane and 100 ml of saturated sodium bicarbonate solution. The organic phase was separated, washed twice with water, dried over sodium sulfate and concentrated to 3.2 g of a semi-solid. This material was taken up in 400 ml of ether, filtered from a small amount of insolubles, and treated dropwise, with good stirring, with 20 ml of saturated ethereal hydrogen chloride. The initial slightly gummy precipitate formed a nice amorphous solid (1.7 g, 55% yield) after stirring for 1 hour. This material was purified by crystallization from 5 ml of ethanol to which 400 ml of ether was added. This afforded 1.10 g (36% overall yield) of (1'α,2'β)-2'-Dimethylaminomethylspiro[5,6,7-trichlorobenzofuran-2(3H),-1'-cyclohexane ] Hydrochloride, m.p. 225°–228°.

ANALYSIS

Calculated for $C_{16}H_{20}Cl_3NO \cdot HCl$: 49.90%C, 5.50%H, 3.64%N, 36.82%Cl, Found: 49.90%C, 5.64%H, 3.47%N, 36.55%Cl.

EXAMPLE 30

(1'β,2'β)-2'-Dimethylaminomethylspiro[5,6-dichlorobenzofuran-2(3H),1'-cyclohexane] Hydrochloride A stirred solution of 6.32 g of (1'β,2'β)-2'-dimethylaminomethylspiro[6-chlorobenzofuran-2(3H),1-cyclohexane] hydrochloride and 2.94 g of N-chlorosuccinimide in 150 ml of absolute methanol was refluxed for 1.0 hour. The solvent was removed under reduced pressure and the residue was partitioned between 200 ml dichloromethane and 200 ml of saturated sodium bicarbonate solution. The aqueous phase was separated and extracted with 100 ml of dichloromethane. The combined organic phases were washed once with water, once with brine, dried over Na₂SO₄ and concentrated in vacuo to an oil weighing 5.8 g (92%). This was converted to the hydrochloride salt by dissolving it in 20 ml of absolute ethanol, cooling to 0° C., and then adding 20 ml of saturated ethereal HCl, with good stirring. An additional 20 ml of ether was added to increase crystallization of the product. After collection and drying, the salt weighed 5.3 g (76% overall yield) and had m.p. 273°–274° dec. Recrystallization from ethanol-ether afforded 2.9 g of (1'β,2'β)-2'-Dimethylaminomethylspiro[5,6-dichlorobenzofuran-2(3H),1'-cyclohexane] Hydrochloride, m.p.275°–277° dec.

ANALYSIS

Calculated for $C_{16}H_{21}Cl_2NO \cdot HCl$: 54.80%C, 6.32%H, 3.99%N, Found: 54.82%C, 6.34%H, 3.77%N.

EXAMPLE 31

(1'β,2'β)-2'-Dimethylaminomethylspiro[5-iodobenzofuran-2(3H),1'-cyclohexane] Hydrochloride To a vigorously stirred two phased mixture of 10.0 g of (1'β,2'β)-2'-dimethylaminomethylspiro[benzofuran-2(3H),1'-cyclohexane] hydrochloride in 200 ml of H₂O and 100 ml of CH₂Cl₂ was added approximately 15.0 g of ICl. Vigorous stirring was continued for 3 hours and then the aqueous phase was basified with 2.5M NaOH. The separated aqueous phase was washed twice with CH₂Cl₂ and the combined organic phases were washed with saturated sodium bisulfite followed by brine and dried over Na₂SO₄. Concentration in vacuo provided 15.4 g (100% yield) of a solid. Further purification was afforded by formation of the hydrochloride salt. To this end the above solid was dissolved in 200 ml of absolute ethanol. On cooling the ethanol, 4.3 g of the solid crystallized. The mother liquor was then acidified with ethanol saturated with hydrogen chloride. The addition of 100 ml of ether and stirring provided 4.85 g (50% yield) of the hydrochloride salt. Recrystallization from ethanol gave 2.7 g (28% yield) of (1'β,2'β)-2'-Dimethylaminomethylspiro[5-iodobenzofuran-2(3H),1'-cyclohexane] hydrochloride, m.p. 244°–246° C.

ANALYSIS

Calculated for $C_{16}H_{22}INO \cdot HCl$: 47.13%C, 5.69%H, 3.44%N, Found: 46.62%C, 5.60%H, 3.21%N.

EXAMPLE 32

(1'β,2'β)-2'-Dimethylaminomethylspiro[5-bromo-7-chlorobenzofuran-2(3H),1'-cyclohexane] Hydrochloride To a stirred solution of 8.9 g of (1'β,2'β)-2'-dimethylamino-methylspiro[5-bromobenzofuran-2(3H),1'-cyclohexane] hydrochloride in 100 ml of methanol was added 37 g of N-chlorosuccinimide (N.C.S.). This solution was refluxed for one hour and then cooled to room temperature and stripped of methanol to an oily residue. The residue was taken up in 150 ml of $CH_2Cl_2$ and 150 ml $H_2O$. The aqueous layer was made basic with a 2.5M NaOH solution. The separated aqueous phase was washed with an additional 100 ml of $CH_2Cl_2$. The combined organic phases were washed with brine and dried over $Na_2SO_4$ followed by concentration in vacuo to 8.5 g (96% yield) of an oil. Purification of the oil was afforded via the hydrochloride salt. To this end the above oil was dissolved in 30 ml of absolute ethanol and cooled in an ice bath. The solution was acidified with a solution of ether saturated with hydrogen chloride. The addition of 100 ml of ether and stirring for 15 minutes produced a solid which was collected giving 6.8 g (70% yield) of crude hydrochloride salt, m.p. 233°–235° C. Recrystallization from 4:1 ether/ethanol solution gave 4.1 g (42% yield) of (1'β,2'β)-2'-Dimethylaminomethylspiro[5-bromo-7-chlorobenzofuran-2(3H)1'-cyclohexane] Hydrochloride, m.p. 239°–241° C.

ANALYSIS

Calculated for $C_{16}H_{21}BrClNO \cdot HCl$: 48.63%C, 5.61%H, 3.54%N, Found: 48.52%C, 5.52%H, 3.47%N.

EXAMPLE 33

(1'β,2'β)-2'-Dimethylaminomethylspiro[7-chlorobenzofuran-2(3H),1'-cyclohexane] Hydrochloride To a stirred solution of 8.0 ml of 2.2M n-butyl lithium in hexane dissolved in 50 ml of THF at −60° C. was added slowly via a double tipped needle a solution of 5.0 g of (1'β,2'β)-2'-dimethylaminomethylspiro[5-bromo-7-chlorobenzofuran-2(3H),1-cyclohexane] in 100 ml of THF. This produced a yellow solution which was stirred at −60° C. for 1½ hr., followed by quenching with 1½ ml of $H_2O$. After stirring 15 minutes at room temperature, the solution was concentrated in vacuo and the residue was taken up in 300 ml of ether and washed with 200 ml of brine. The separated ether layer was dried over $Na_2SO_4$ and concentrated in vacuo to give 3.2 g (83% yield) of an oil. Purification via the hydrochloride salt was afforded by dissolving the above oil in a mixture of 15 ml of ethanol and 25 ml of anhydrous ether. To this cooled solution was added dropwise a solution of ether saturated with hydrogen chloride until the solution became acidic. Addition of 125 ml of ether and stirring for ½ hour produced 2.6 g (59% yield) of off white solid, m.p. 236°–239° C. Recrystallization from ethyl acetate/methanol gave 2.1 g (48% yield) of (1'β,2'β)-2'-Dimethylaminomethylspiro[7-chlorobenzofuran-2(3H),1'-cyclohexane] hydrochloride, m.p. 237°–239° C.

ANALYSIS

Calculated for $C_{16}H_{22}ClNO \cdot HCl$: 60.76%C, 7.33%H, 4.43%N, Found: 60.71%C, 7.29%H, 4.20%N.

EXAMPLE 34

(1'β,2'β)-2'-N-Ethoxycarbonyl-N-methylaminomethylspiro[benzofuran-2(3H),1'-cyclohexane]

To a stirred mixture, under $N_2$, of 9.82 g of (1'β,2'β)-2'-dimethylaminomethylspiro[benzofuran-2(3H),1'-cyclohexane] and 8.40 g of sodium bicarbonate in 75 ml of dry benzene, was added dropwise, 6.57 g of ethyl chloroformate dissolved in 25 ml of benzene. After the addition was completed (15 minutes), the mixture was refluxed overnight (16 hours). The reaction was then cooled and 100 ml of water was added, with good stirring. The layers were separated, and the organic phase was washed with dilute NaOH, with dilute HCl, and finally with brine. After drying over $Na_2SO_4$, the solvent was removed leaving an oil.

For purification this was dissolved in 25 ml of hexane and absorbed on a tall chromatography column containing 500 g of silica gel made up in hexane. Elution first with hexane, then with increasing percentages (20% per step) of toluene in hexane, followed by increasing percentages (20% per step) of chloroform in toluene, and finally with 100% chloroform brought forth 4.88 g (42% overall yield) of (1'β,2'β)-2'-N-Ethoxycarbonyl-N-methylaminomethylspiro[benzofuran-2(3H),1'-cyclohexane] as an oil.

ANALYSIS

Calculated for $C_{18}H_{25}NO_3$: 71.26%C, 8.30%H, 4.61%N, Found: 71.15%C, 8.30%H, 4.50%N.

EXAMPLE 35

(1'β,2'β)-2'-N-Ethoxycarbonyl-N-methylaminomethylspiro[5-nitrobenzofuran-2(3H),1'-cyclohexane]

To a stirred solution of 25.0 g of (1'β,2'β)-N-ethoxycarbonyl-N-methylaminomethylspiro[benzofuran-2(3H),1'-cyclohexane] in 250 ml glacial acetic acid was added dropwise 10.0 ml. of 70% $HNO_3$ in 150 ml of glacial acetic acid. The reaction was heated to 100° C. and maintained at this temperature for 10 minutes. The reaction mixture was cooled and poured into 1000 ml of ice water and extracted with 600 ml $CH_2Cl_2$. The separated aqueous layer was extracted thrice with 200 ml $CH_2Cl_2$. The organic layers were combined and made basic with 2.5M NaOH. The separated organic layer was washed with brine, dried over $MgSO_4$, and concentrated in vacuo to give 37.8 g of an oil. This oil was purified by dissolving it in $CH_2Cl_2$ and eluting it through a short pad of alumina. Concentration of the eluant gave 15.8 g (a 53% yield) of an oil, which was crystallized by trituration with petroleum ether. The resulting solid of (1'β,2'β)-2'-N-Ethoxycarbonyl-N-methylaminomethylspiro[5-nitrobenzofuran-2(3H),1'-cyclohexane] after drying had a m.p. 105°–107° C.

ANALYSIS

Calculated for $C_{18}H_{24}N_2O_5$: 62.05%C, 6.94%H, 8.04%N, Found: 62.19%C, 6.97%H, 8.08%N.

EXAMPLE 36

(1'β,2'β)-2'-N-ethoxycarbonyl-N-methylaminomethylspiro[5-aminobenzofuran-2(3H),1'-cyclohexane] Oxalate A Parr flask, charged with 1.2 g of 5% palladium on charcoal, 9.5 g of (1'β,2'β)-2'-N-ethoxycarbonyl-N-methylaminomethylspiro[5-nitrobenzofuran-2(3H),1'-cyclohexane] and 125 ml of methanol was shaken under 52 lbs. of $H_2$ for 3 hours. The catalyst was then removed by filtration and the mother liquor concentrated in vacuo to give 7.8 g (90% yield) of an oil. This residue was purified via the oxalate salt. To this end, 5.2 g of the residue was dissolved in 70 ml of anhydrous ether and cooled in an ice bath. To this was added dropwise a solution of 1.5 g of oxalic acid in 200 ml of anhydrous ether. The resulting solid was collected and washed well with ether and dried under vacuum to give 4.3 g (66% yield) of a solid, m.p. 97°–101° C. This solid was recrystallized from a 2:1, ether/ethyl acetate solution to give 3.6 g (55% yield) of (1'β,2'β)-2'-N-ethoxycarbonyl-N-methylaminomethylspiro[5-aminobenzofuran-2(3H),1'-cyclohexane] Oxalate salt, m.p. 103°–105° C.

ANALYSIS

Calculated for $C_{18}H_{26}N_2O_3 \cdot C_2H_2O_4$: 58.81%C, 6.91%H, 6.86%N, Found: 58.08%C, 6.88%H, 6.60%N.

EXAMPLE 37

(1'β,2'β)-2'-N-Ethoxycarbonyl-N-methylaminomethylspiro[5-dimethylaminobenzofuran-2(3H),1'-cyclohexane] Hydrochloride A Parr flask was charged with 3.0 g of 5% palladium on charcoal, 5.1 g of (1'β,2'β)-2'-N-ethoxycarbonyl-N-methylaminomethylspiro[5-nitrobenzofuran-2(3H),1'-cyclohexane] in 50 ml of methanol and 50 ml of 2-ethoxyethanol followed by the addition of 25 ml of a 37% aqueous formaldehyde solution. This mixture was put on a Parr shaker under 40 lbs. of $H_2$ and shaken for 4 hours. This procedure was repeated a second time using the exact amounts as stated above. The two mixtures were then filtered and the combined mother liquors were concentrated in vacuo to give 10.0 g (100% yield) of an oil. This oil was dissolved in 15 ml of absolute ethanol and 50 ml of anhydrous ether and subsequently cooled in an ice bath. To this cooled solution was added a solution of ether saturated with hydrogen chloride until pH paper indicated the solution was acidic. Seeding and the addition of 250 ml of ether provided the solid hydrochloride salt which was collected and dried to give 4.2 g of a solid. This solid was recrystallized from an ethanol/ether solution to give 2.3 g (21% yield) of (1'β,2'β)-2'-N-Ethoxycarbonyl-N-methylaminomethylspiro[5-dimethylaminobenzofuran-2(3H),1'-cyclohexane] Hydrochloride, m.p. 171°–173° C.

ANALYSIS

Calculated for $C_{20}H_{30}N_2O_3 \cdot HCl$: 62.73%C, 8.16%H, 7.32%N, Found: 62.72%C, 8.34%H, 7.16%N.

EXAMPLE 38

(1'β,2'β)-2'-Dimethylaminomethylspiro[5-aminobenzofuran-2(3H),1'-cyclohexane] Dihydrochloride To a mixture of 3.8 g of lithium aluminum hydride (LAH) in 250 ml of anhydrous ethyl ether was added dropwise a solution of 10.7 g of (1'β,2'β)-2'-N-ethoxycarbonyl-N-methylaminomethylspiro[5-aminobenzofuran-2(3H),1'-cyclohexane] in 250 ml of ethyl ether. Addition of the carbamate was completed within 1 hour. This mixture was stirred an additional 2.5 hours after complete addition and then cautiously quenched with 50 ml of saturated $Na_2SO_4$. The organic phase was decanted from the gelatinous aqueous phase and further dried over $Na_2SO_4$. The solution was concentrated in vacuo to give 8.3 g (94% yield) of an oil. This oil was converted to the dihydrochloride salt by dissolving it in 100 ml of absolute ethanol, and cooling it in an ice bath and adding a solution of ether saturated with hydrogen chloride dropwise until the solution became strongly acidic. The solid dihydrochloride salt, 8.65 g (76% yield) was collected after the addition of 300 ml of fresh ether. This crude salt was recrystallized twice: once in an ethanol/ether solution and again in an ethyl acetate/ether solution to give 2.6 g (23% yield) of (1'β,2'β)-2'-Dimethylaminomethylspiro[5-aminobenzofuran-2(2H),1'-cyclohexane]dihydrochloride, m.p. 279°–281° C.

ANALYSIS

Calculated for $C_{16}H_{24}N_2O \cdot 2HCl$: 57.66%C, 7.86%H, 8.40%N, Found: 57.54%C, 7.93%H, 8.19%N.

EXAMPLE 39

(1'β,2'β)-2'-dimethylaminomethylspiro[5-dimethylaminobenzofuran-2(3H),1-cyclohexane]-dihydrochloride Utilizing the same procedure described in Example 38, (1'β,2'β)-2'-dimethylaminomethylspiro[5-dimethylaminobenzofuran-2(3H),1-cyclohexane]-dihydrochloride was prepared from (1'β,2'β)-2'-N-ethoxycarbonyl-N-methylaminomethylspiro[5-dimethylaminobenzofuran-2(3H),1'-cyclohexane]hydrochloride.

EXAMPLE 40

(1'β,2'β)-N-Ethoxycarbonyl-N-methylaminomethylspiro[5-chlorobenzofuran-2(3H),1'-cyclohexane]

To a stirred mixture under nitrogen, of 11.2 g of (1'β,2'β)-2'-dimethylaminomethylspiro[5-chlorobenzofuran-2(3H),1'-cyclohexane] and 13.8 g of anhydrous potassium carbonate in 150 ml of dry benzene was added dropwise a solution of 8.68 g of ethyl chloroformate in 25 ml of benzene. The addition took 0.5 hours and then the mixture was brought to reflux. After 2 hours, an additional charge of 8.68 g of ethyl chloroformate and 13.8 g of potassium carbonate was added and refluxing was continued overnight. The mixture was then cooled and 200 ml of ice-water was added over a 5 minute period, with vigorous stirring. Then 200 ml of ether was added, and the layers were separated. The organic phase was washed with dilute brine, twice with 2N-hydrochloric acid, and again with dilute brine. After drying over anhydrous sodium sulfate, the solvent was removed in vacuo leaving 13.9 g (100% yield) of an oil. For purification, 12 g of the oil was dissolved in 50 ml of toluene and adsorbed on a tall chromatography column containing 600 g of silica gel made up in hexane. Elution first with hexane, then with increasing percentages (10% per step) of toluene in hexane, followed by increasing percentages (10% per step) of chloroform in toluene and finally with 100% chloroform brought forth 5.7 g (48% yield) of (1'β,2'β)-N-Ethoxycarbonyl-N-methylaminomethylspiro[5-chlorobenzofuran-2(3H),1'-cyclohexane] as an oil.

ANALYSIS

Calculated for $C_{18}H_{24}ClNO_3$: 63.99%C, 7.16%H, 4.13%N, Found: 63.80%C, 7.15%H, 4.06%N.

EXAMPLE 41

(1'β,2'β)-N-Ethoxycarbonyl-N-methylaminomethyl-spiro[5-chlorobenzofuran-2(3H),1'-cyclohexane]

To a stirred mixture under nitrogen, of 44.8 g of (1'α,2'β)-2'-dimethylaminomethylspiro[5-chlorobenzofuran-2(3H),1'-cyclohexane] and 55.3 g of anhydrous potassium carbonate in 450 ml of dry toluene was added dropwise 26.0 g of ethyl chloroformate. After the addition was completed the mixture was refluxed for 6 hours when an additional charge of 13.0 g was added. After refluxing overnight (16 hours) the mixture was cooled and 250 ml of ice-water was added over a 5 minute period, with good stirring. Then 500 ml of ether was added, and the layers were separated. The organic phase was washed twice with dilute sodium hydroxide solution, with dilute hydrochloric acid, and finally with dilute brine. After drying over anhydrous sodium sulfate, the solvent was removed in vacuo leaving 44.0 g (81% yield) of an oil.

For purification, 12.0 g of the oil was dissolved in 50 ml of toluene, and adsorbed on a tall chromatography column containing 600 g of silica gel made up in hexane. Elution first with hexane, then with increasing percentages (10% per step) of toluene in hexane, followed by increasing percentages (10% per step) of chloroform in toluene, and finally with 100% chloroform brought forth 6.1 g (41% overall yield) of (1'α,2'β)-N-Ethoxycarbonyl-N-methylaminomethylspiro[5-chlorobenzofuran-2(3H),1'-cyclohexane] as an oil.

ANALYSIS

Calculated for $C_{18}H_{24}ClNO_3$: 63.99%C, 7.16%H, 4.13%N, Found: 64.08%C, 7.12%H, 3.82%N.

EXAMPLE 42

(1'β,2'β)-2'-N-Methylaminomethylspiro[benzofuran-2(3H),1'-cyclohexane]Hydrochloride A stirred mixture of 9.1 g of (1'β,2'β)-2'-N-ethoxycarbonyl-N-methylaminomethylspiro[benzofuran-2(3H),1'-cyclohexane], 5.61 g of potassium hydroxide, 25 ml of water and 100 ml of 1-butanol was refluxed under nitrogen for 5 days, then concentrated to a syrupy residue. This was partitioned between ether and water. The aqueous layer was separated and extracted once more with ether. The combined ether extracts were washed twice with dilute brine, dried over sodium sulfate, and concentrated to an oil. This was dissolved in 25 ml of ethanol and treated with 50 ml of ethereal hydrogen chloride. An additional 50 ml of ether was added to maximize precipitation. The solid was filtered, washed once with 1:4 ethanol:ether, twice with ether, and dried to afford 2.5 g (31% overall yield) of product, m.p. 243°–245°. Recrystallization from ethanol-ether furnished 2.2 g of (1'β,2'β)-2'-N-Methylaminomethyl-spiro[benzofuran-2(3H),1'-cyclohexane]Hydrochloride, m.p. 244°–246°.

ANALYSIS

Calculated for $C_{15}H_{21}NO \cdot HCl$: 67.28%C, 8.28%H, 5.23%N, Found: 67.30%C, 8.13%H, 5.22%N.

EXAMPLE 43

(1'β,2'β)-2'-N-Methylaminomethylspiro[5-chlorobenzofuran-2(3H),-1'-cyclohexane]Hydrochloride A stirred mixture of 16.9 g of (1'β,2'β)-N-ethoxycarbonyl-N-methylaminomethylspiro[5-chlorobenzofuran-2(3H),1'-cyclohexane], 14.0 g of potassium hydroxide, 35 ml of water and 450 ml of 1-butanol was refluxed under nitrogen for 3 days, whereupon an additional charge of 7.0 g of potassium hydroxide was added. After a total of 5 days at reflux, the reaction fluid was concentrated on the rotovac to a syrupy residue. This was partitioned between ether and water. The aqueous layer was separated and extracted once more with ether. The combined ether extracts were washed twice with dilute brine, dried over sodium sulfate, and concentrated to an oil. This was dissolved in 25 ml of ethanol, cooled to 0°, and treated dropwise with 50 ml of saturated ethereal hydrogen chloride over 15 minutes. An additional 125 ml of ether was then added in portions to maximize precipitation. The hydrochloride salt was filtered, washed once with 1:4 ethanol:ether, twice with ether, and dried to afford 6.3 g (42% overall yield) of product, m.p. 237°–239°. Recrystallization from ethanol-ether furnished 5.2 g of (1'β,2'β)-2'-N-Methylaminomethylspiro[5-chlorobenzofuran-2(3H),1—cyclohex-ane]Hydrochloride, m.p. unchanged.

ANALYSIS

Calculated for $C_{15}H_{20}ClNO \cdot HCl$: 59.60%C, 7.00%H, 4.63%N, Found: 59.45%C, 7.10%H, 4.51%N.

EXAMPLE 44

(1'α,2'β)-2'-N-Methylaminomethylspiro[5-chlorobenzofuran-2(3H),1'-cyclohexane]Hydrochloride A stirred mixture of 27.0 g of (1'α,2'β)-N-ethoxycarbonyl-N-methylaminomethylspiro[5-chlorobenzofuran-2(3H),1'-cyclohexane], 22.4 g of potassium hydroxide, 30 ml of water and 700 ml of 1-butanol was refluxed under nitrogen for 3 days, whereupon an additional charge of 11.2 g of potassium hydroxide was added. After a total of 5 days at reflux, the reaction fluid was concentrated on a rotovac to a syrupy residue. This was partitioned between ether and water. The aqueous layer was separated and extracted once more with ether. The combined ether extracts were washed twice with dilute brine, dried over sodium sulfate, and concentrated to an oil. This was dissolved in 25 ml of ethanol, cooled to 0° with stirring, and treated dropwise with 100 ml of saturated ethereal hydrogen chloride over 15 minutes. An additional 100 ml of ether was then added in portions to maximize precipitation. The hydrochloride salt was filtered, washed once with 1:9 ethanol:ether, twice with a small volume of acetone, twice with ether, and dried to afford 7.4 g (31% overall yield) of essentially pure (by TLC) salt. Two recrystallizations from ethanol-ether (charcoal) furnished 4.85 g (20% overall yield) of (1'α,2'β)-2'-N-Methylaminomethylspiro[5-chlorobenzofuran-2(3H),1'-cyclohexane]Hydrochloride, m.p. 168°–171°.

ANALYSIS

Calculated for $C_{15}H_{20}ClNO \cdot HCl$: 59.60%C, 7.00%H, 4.63%N, Found: 59.79%C, 6.94%H, 4.49%N.

EXAMPLE 45

(1'α,2'β)-2'-N-Cyano-N-methylaminomethylspiro[benzofuran-2(3H),1'-cyclohexane]

To a well stirred solution under $N_2$ of 9.7 g of BrCN in 400 ml dry benzene was added 40.0 g of anhydrous $K_2CO_3$ in one portion. This mixture was stirred for 15 minutes whereupon a slow dropwise addition of 15.0 g of (1'α,2'β)-2-dimethylaminomethylspiro[benzofuran-2(3H),1'-cyclohexane] in 200 ml dry benzene was started. After complete addition (1.75 hours) the mixture was set to reflux for 2 hours. The reaction mixture was then cooled, filtered and concentrated in vacuo to a residue, which was dissolved in 250 ml methanol and refluxed for 15 minutes to assure degradation of the residual BrCN. After cooling, the methanol solution was concentrated in vacuo to give 16.0 g of a crude solid. The solid was then taken up in 600 ml ether and extracted with 300 ml of dilute NaOH, 250 ml of dilute HCl, and 250 ml saturated brine, dried over anhydrous sodium sulfate and concentrated in vacuo to yield 16.0 g of product. Further purification was achieved by two recrystallizations from hexane-ether to give 4.5 g (30% yield) of (1'α,2'β)-2'-N-Cyano-N-methylaminomethylspiro[benzofuran-2(3H),1'-cyclohexane], m.p. 105.5°–107° C.

ANALYSIS

Calculated for $C_{16}H_{20}N_2O$: 74.97%C, 7.86%H, 10.93%N, Found: 74.96%C, 7.94%H, 11.00%N.

EXAMPLE 46

(1'α,2'β)-2'-N-Methylaminomethylspiro[benzofuran-2(3H),1'-cyclohexane]Hydrochloride To a stirred mixture under $N_2$, of 5.0 g of $LiAlH_4$ and 200 ml of dry THF was added a solution of 11.16 g of (1'α,2'β)-2'-N-cyano-N-methylaminomethylspiro[benzofuran-2(3H),1'-cyclohexane] in 150 ml of dry THF. After complete addition (0.5 hr.) the mixture was refluxed for 2 hours. The solution was then cooled in an ice bath to 5° C. and quenched by a continuous addition of 25 ml of saturated $Na_2SO_4$. The mixture was suction filtered and the filtrate dried over anhydrous sodium sulfate, and concentrated in vacuo to yield 12.4 g of an oil. The hydrochloride salt was prepared by dissolving the above oil in 75 ml of absolute ethanol. The ethanol solution was cooled in an ice bath and then 20 ml of ether saturated with hydrogen chloride was added. After the addition of 25 ml of anhydrous ether, the precipitated hydrochloride salt was collected and dried. The pure solid 3.0 g (26% yield) of (1'α,2'β)-2'-N-Methylaminomethylspiro[benzofuran-2(3H),1'-cyclohexane]Hydrochloride was obtained after a second recrystalization from ethanol-ether, m.p. 255.5°–257° C.

ANALYSIS

Calculated for $C_{15}H_{21}NO \cdot HCl$: 67.28%C, 8.28%H, 5.23%N, Found: 67.39%C, 8.09%H, 5.18%N.

EXAMPLE 47

(a)

cis-1-(2-Fluorobenzyl)-2-dimethylaminocyclohexan-1-ol Oxalate

To a stirred mixture, under $N_2$, of 11.7 g of magnesium turnings and 200 ml of anhydrous ether was added dropwise a solution of 69.4 g of 2-fluorobenzyl chloride in 200 ml of ether. After an initial charge of 25 ml in one portion, Grignard reaction began to take place, spontaneously bringing the ether to reflux. The rate of addition and occasional cooling maintained the reaction temperature at about 30° during the 0.45 hour addition period. The mixture containing the Grignard reagent was then cooled and kept between 15°–20° during the addition over 1.25 hours of a solution of 56.5 g of 2-dimethylaminocyclohexanone in 150 ml of ether. After 2 hours, the mixture was cooled and kept at 0°–10° while being quenched by addition of 200 ml of ammonium chloride solution. Water was then added to dissolve the salts. The aqueous phase was separated from the ether layer and reextracted with two 250 ml portions of ether. The combined ether layers were washed once with ammonium chloride solution, once with dilute brine, dried over anhydrous sodium sulfate, and concentrated in vacuo to an oil weighing 67.7 g. An analysis of this material by TLC indicated it contained 30% of unreacted starting ketone, and so this material was resubmitted to another Grignard reaction, exactly as described above. After workup as above, 47 g (47% crude yield) of oil was obtained in which there was only a trace of starting material. This oil was purified as the oxalate salt as follows. Part of the above oil (32.0 g) was dissolved in 200 ml of ether, and with good stirring, treated with a solution of 11.4 g of oxalic acid in 1200 ml of ether over a 5 minute period. After 2 hours, the crystals were filtered, washed with ether and dried to afford 37 g (85%) of product. Recrystallization from 160 ml of ethanol provided 23.3 g (54% overall yield) of cis-1-(2-Fluorobenzyl)-2-dimethylaminocyclohexan-1-ol Oxalate m.p. 154°–156°.

ANALYSIS

Calculated for $C_{15}H_{22}FNO \cdot C_2H_2O_4$: 59.81%C, 7.09%H, 4.10%N, Found: 59.79%C, 7.14%H, 4.01%N.

(b) The hydrochloride salt was prepared. To this end, the above oxalate salt was reversed back to the pure free base of the alcohol. This was dissolved in ethanol and treated with ether saturated with hydrogen chloride. The resulting HCl salt (92% yield) had an m.p. 216°–218°. Recrystallization from ethanol-ether afforded the pure alcohol hydrochloride salt in 80% overall yield, m.p. unchanged at 116°–218°.

ANALYSIS

Calculated for $C_{15}H_{22}FNO \cdot HCL$: 62.58%, 8.06%H, 4.83%N, Found: 62.53%C, 8.02%H, 4.79%N.

EXAMPLE 48 cis-1-(5-Chloro-2-fluorobenzyl)-2-dimethylaminocyclohexane-1-ol Hydrochloride

The procedure of Example 47 was repeated except that 5-chloro-2-fluorobenzyl chloride was employed to obtain cis-1-(5-Chloro-2-fluorobenzyl)-2-dimethylaminocyclohexane-1-ol Hydrochloride.

EXAMPLE 49

(1'β,2'β)-2'-Dimethylaminospiro[benzofuran-2(3H),1'-cyclohexane]Hydrochloride

To a well stirred solution, under nitrogen of 6.8 g of cis-1-(2-Fluorobenzyl)-2-dimethylaminocyclohexan-1-ol, and 120 ml of benzene was added 2.5 g of 61% NaH in an oil dispersion, followed by 30 ml of dry dimethylformamide (DMF). This mixture was refluxed for 8½ hours at which time it was cooled and poured into 400 ml of ice and water and extracted with 500 ml of ether. The separated aqueous phase was washed twice with 100 ml of ether and the combined organic layers were washed with brine and dried over $Na_2SO_4$. Concentration in vacuo provided 4.9 g (82% yield) of an oil. Further purification was afforded by formation of the hydrochloride salt. To this end, the above oil was dissolved in a mixture of 15 ml of absolute ethanol and 50 ml of ether. The cooled solution was acidified with ether saturated with hydrogen chloride. The addition of 150 ml of ether along with stirring provided 2.9 g (40% yield) of a solid. Successive recrystallizations from isopropanol gave 2.0 g (28% yield) of (1'β,2'β)-2'-Dimethylaminospiro[benzofuran-2(3H),1'-cyclohexane]Hydrochloride, m.p. 228°-230° C.

ANALYSIS

Calculated for $C_{15}H_{21}NO·HCl$: 67.28%C, 8.28%H, 5.23%N, Found: 67.41%C, 8.24%H, 5.24%N.

EXAMPLE 50

(1'β,2'β)-2'-Dimethylaminospiro[5-bromobenzofuran-2(3H),1'-cyclohexane]Hydrochloride To a stirred solution of 5.0 g of (1'β,2'β)-2'-dimethylaminospiro[benzofuran-2(3H),1'-cyclohexane]hydrochloride in 100 ml of methanol was added 3.6 g of N-bromosuccinimide. The mixture was stirred at room temperature for 0.5 hours and then concentrated in vacuo. The resultant liquid was taken up in 150 ml of $CH_2Cl_2$ and 200 ml of $H_2O$ and subsequently basified with 2.5M NaOH. The separated aqueous layer was washed twice with 50 ml of $CH_2Cl_2$ and the combined organic layers were washed with brine and dried over $Na_2SO_4$. Concentration of the organic phase in vacuo provided 5.05 g (97% yield) of an oil. Further purification of this oil was afforded by formation of the hydrochloride salt. To this end, the above oil was dissolved in a mixture of 25 ml of absolute ethanol and 75 ml of ether and cooled in an ice bath. The cooled solution was acidified with ether saturated with hydrogen chloride and addition of 100 ml of fresh ether gave 3.3 g (51% yield) of solid hydrochloride salt. Recrystallization from an ethanol/ether solution gave 2.7 g (42% yield) of (1'β,2'β)-2'-Dimethylaminospiro[5-bromobenzofuran-2(3H),1'-cyclohexane]Hydrochloride, m.p. 232°-234° C.

ANALYSIS

Calculated for $C_{15}H_{20}BrNO·HCl$: 51.97%C, 6.11%H, 4.04%N, Found: 52.08%C, 6.06%H, 4.00%N.

EXAMPLE 51

(1'β,2'β)-2'-Dimethylaminospiro[5-chlorobenzofuran-2(3H),1'-cyclohexane]Hydrochloride The procedure of Example 49 was repeated except that cis-1-(5-chloro-2-fluorobenzyl)-2-dimethylaminocyclohexan-1-ol was employed to obtain (1'β,2'β)-2'-Dimethylaminospiro[5-chlorobenzofuran-2(3H),1'-cyclohexane]Hydrochloride.

EXAMPLE 52

(1'β,2'β)-2'-Dimethylaminospiro[5-iodobenzofuran-2(3H),1'-cyclohexane]Hydrochloride The procedure of Example 50 was repeated except that iodochloride instead of N-bromosuccinide was employed to obtain (1'β,2'β)-2'-Dimethylaminospiro[5-iodobenzofuran-2(3H),1'-cyclohexane]Hydrochloride.

EXAMPLE 53

Cis-1-(2-Fluorobenzyl)-2-(cyanomethyl)cyclohexan-1-ol

To a stirred mixture, under $N_2$, of 10.3 g of magnesium turnings in 100 ml of anhydrous ether was added dropwise a solution of 56.8 g of 2-fluorobenzyl chloride in 150 ml of ether. When the first few mls. were charged, the reaction began to take place, exothermically bringing the ether to reflux. This temperature was maintained by the rate of addition (0.75 hr.). When the Grignard-forming reaction was complete, the mixture was aged for 1.5 hours and then added via a double-tipped needle to a solution of 49.0 g of 2-oxo-cyclohexane acetonitrile in 300 ml of ether. The addition of the Grignard reagent was completed in 0.5 hours and thereafter the mixture was stirred at room temperature for 0.5 hours. The mixture was cooled and quenched with 120 ml of saturated $NH_4Cl$. The organic phase was decanted from the resulting gelatinous material and concentrated in vacuo to give 71.65 g (81% yield) of an oil. Further purification was afforded by column chromatography. To this end the crude alcohol was eluted through silica gel with toluene containing 1% methanol. The purified alcohol was crystallized by trituration with hexane to provide cis-1-(2-Fluorobenzyl)-2-(cyanomethyl)cyclohexan-1-ol, m.p. 61°-63° C.

ANALYSIS

Calculated for $C_{15}H_{18}FNO$: 72.85%C, 7.34%H, 5.66%N,
Found: 73.00%C, 7.40%H, 5.49%N.

EXAMPLE 54 cis-1-(5-chloro-2-fluorobenzyl)-2-(cyanomethyl)cyclohexan-1-ol

The procedure of Example 53 was repeated except that 5-chloro-2-fluorobenzyl chloride was employed to obtain cis-1-(5-chloro-2-fluorobenzyl)-2-cyanomethyl)-cyclohexan-1-ol.

EXAMPLE 55

(1'β,2'β)-2'-Cyanomethylspiro[benzofuran-2(3H),1'-cyclohexane]

A stirred mixture under $N_2$ of 24.2 g of cis-1-(2-fluorobenzyl)-2-(cyanomethyl)cyclohexan-1-ol and 4.0 g of 60% sodium hydride in an oil dispersion in 500 ml of benzene and 750 ml of dimethylformamide was refluxed for 21 hours. The mixture was then carefully decanted into ice water with good stirring. Then 1000 ml of ether was added to extract the product. The phases were separated and the aqueous layer was extracted twice more than 500 ml of ether. The combined organic phases were washed with brine, dried over sodium sulfate and concentrated in vacuo to afford 15.4 g (69% yield) of (1'β,2'β)-2'-Cyanomethylspiro[benzofuran-2(3H),1'-cyclohexane] as an oil.

EXAMPLE 56

(1'β,2'β)-2'-Cyanomethylspiro[5-chlorobenzofuran-2(3H),1'-cyclohexane]

The procedure of Example 55 was repeated except that cis-1-(5-chloro-2-fluorobenzyl)-2-(cyanomethyl)-cyclohexane-1-ol was employed to obtain (1'β,2'β)-2'-Cyanomethylspiro[5-chlorobenzofuran-2(3H),1'-cyclohexane].

EXAMPLE 57

(1'β,2'β)-2'-Aminoethylspiro[benzofuran-2(3H),1'-cyclohexane] Hydrochloride

To a stirred mixture, under N$_2$, of 5.0 g of 50% LiAlH$_4$ in an oil dispersion and 150 ml of anhydrous ethyl ether was added dropwise a solution of 4.0 g of (1'β,2'β)-2'-cyanomethylspiro [benzofuran-2(3H),1'-cyclohexane] in 100 ml of ether. This mixture was stirred at room temperature for 2 hours and then cooled in ice and cautiously quenched with 40 ml of a saturated Na$_2$SO$_4$ solution. The organic phase was decanted from the gelatinous aqueous phase and washed with brine and dried over Na$_2$SO$_4$. Concentration in vacuo provided 6.0 g of an oil. Further purification was afforded by formation of the hydrochloride salt. To this end the above oil was dissolved in 100 ml of ether and the solution was cooled, and acidified with ether saturated with hydrogen chloride. The resulting solid was filtered and dried to give 2.8 g of the crude hydrochloride salt. Successive recrystallizations from an ethyl acetate:methanol solution gave 2.0 g of (1'β,2'β)-2'-Aminoethylspiro[benzofuran-2(3H),1'-cyclohexane] Hydrochloride, m.p. 189°–191° C.

ANALYSIS

Calculated for C$_{15}$H$_{21}$NO.HCl: 67.28%C, 8.28%H, 5.23%N,
Found: 67.02%C, 8.15%H, 5.03%N.

EXAMPLE 58

(1'β,2'β)-2'-Aminoethylspiro[5-chlorobenzofuran-2(3H),1'-cyclohexane] Maleate

The procedure of Example 57 was repeated except that (1'β,2'β)-2'-cyanomethyl[5-chlorobenzofuran-2(3H),1'-cyclohexane] was employed to obtain (1'β,2'β)-2'-Aminoethylspiro[5-chlorobenzofuran-2(3H),1'-cyclohexane] Maleate, m.p. 135°–138°.

EXAMPLE 59

(1'β,2'β)-2'-Aminoethylspiro[5-bromobenzofuran-2(3H),1'-cyclohexane] Fumarate

The procedure of Example 50 was repeated except that (1'β,2'β)-2'-Aminoethylspiro[benzofuran-2(3H),1'-cyclohexane] hydrochloride was employed. The pure product, as the fumarate salt, had m.p. 192°–194°.

EXAMPLE 60

(1'β,2'β)-2'-N-ethyoxycarbonylaminoethylspiro[benzofuran-2(3H), 1'-cyclohexane]

To a stirred mixture under N$_2$ of 19.4 of (1'β,2'β)-2'-aminoethylspiro[benzofuran-2(3H),1'-cyclohexane] and 35 g of anhydrous potassium carbonate in 250 ml of dichloromethane was added dropwise a solution of 13.7 g of ethyl chloroformate in 100 ml of dichloromethane. When the addition was completed the mixture was stirred at room temperature overnight (about 16 hours). The salts were then filtered off, and the filtrate was washed with water, with dilute hydrochloric acid, with brine, was dried over sodium sulfate and concentrated in vacuo to afford 19.2 g. This was triturated with ether, filtered, and the filtrate was concentrated in vacuo to afford 11.7 g (46% yield) of (1'β,2'β)-2'-N-ethoxycarbonylaminoethylspiro[benzofuran-2(3H), 1'-cyclohexane].

EXAMPLE 61

(1'β,2'β)-2'-N-ethoxycarbonylaminoethylspiro[5-chlorobenzofuran-2(3H),1'-cyclohexane]

The procedure of Example 60 was repeated except that (1'β,2'β)-2'-aminoethylspiro[5-chlorobenzofuran-2(3H), 1'-cyclohexane] was employed to obtain (1'β,2'β)-2'-N-ethoxycarbonylaminoethylspiro[5-chlorobenzofuran-2(3H),1'-cyclohexane].

EXAMPLE 62

(1'β,2'β)-2'-N-Methylaminoethylspiro[benzofuran-2(3H),1'-cyclohexane] Hydrochloride To a stirred mixture under N$_2$ of 6.0 g of 50% LiAlH$_4$ (protected in oil) in 150 ml of dry THF was added dropwise a solution of 11.7 g of (1'β,2'β)-2'-N-ethoxycarbonylaminoethylspiro[benzofuran-2(3H),1'-cyclohexane] in 100 ml of dry THF (tetrahydrofuran). After complete addition, the mixture was refluxed for 1 hour, then cooled and quenched with saturated Na$_2$SO$_4$ (40 ml). The resulting gelatinous mixture was filtered through celite and the filtrate was concentrated in vacuo to an oil. This oil was extracted into 200 ml of ether and washed with brine. The organic phase was dried over Na$_2$SO$_4$ and concentrated in vacuo to give 10.8 g (100% yield) of an oil. Further purification of the oil was afforded via formation of the hydrochloride salt. To this end the above oil was dissolved in 25 ml of absolute ethanol and 125 ml of anhydrous ether and acidified with a solution of ether saturated with hydrogen chloride. The resultant hydrochloride salt was dried to give 7.55 g (68% yield) of crude salt. Recrystallization from absolute ethanol provided 2.2 g (20% yield) of (1'β,2'β)-2'-N-Methylaminoethylspiro[benzofuran-2(3H),1'-cyclohexane] Hydrochloride, m.p. 250°–252°.

ANALYSIS

Calculated for C$_{16}$H$_{23}$NO.HCl: 68.19%C, 8.58%H, 4.97%N,
Found: 67.91%C, 8.52H, 4.76%N.

EXAMPLE 63

(1'β,2'β)-2'-N-Methylaminoethylspiro[5-chlorobenzofuran-2(3H),1'-cyclohexane] Hydrochloride To a stirred mixture, under N$_2$ of 7.5 g of 48% LAH in an oil dispersion and 100 ml of anhydrous THF was added dropwise a solution of 16.0 g of (1'β,2'β)-2'-N-ethoxycarbonylaminoethylspiro[5-chlorobenzofuran-2(3H),1'-cyclohexane] in 100 ml THF. This mixture was refluxed for 2 hours and then cooled in ice and cautiously quenched with 40 ml of saturated Na$_2$SO$_4$ solution. The resulting mixture was filtered through celite and the filtrate was concentrated in vacuo to an oil. This oil was taken up in 200 ml of ether and washed with brine and dried over Na$_2$SO$_4$. Concentration of the organic phase in vacuo yielded 14.3 g (100% yield) of an oil. Purification of the oil was afforded via formation of the hydrochloric salt. To this end the above oil was dissolved in 50 ml of ether and 10 ml of absolute ethanol. The ice cooled solution was acidified with a solution of ether saturated with hydrogen chloride. The resulting solid was filtered and dried to give 11.2 g (75% yield). Recrystallization of this solid from absolute ethanol provided 3.2 g (22% yield) of (1'β,2'β)-2'-N-Methylaminoethylspiro[5-chlorobenzofuran-2(3H),1'-cyclohexane] Hydrochloride, m.p. 200°-201° C.

ANALYSIS

Calculated for $C_{16}H_{22}ClNO \cdot HCl$: 60.76%C, 7.33%H, 4.43%N,
Found: 60.48%C, 7.19%H, 4.29%N.

EXAMPLE 64

(1'β,2'β)-2'-N-Methylaminoethylspiro[5-bromobenzofuran-2(3H), 1'-cyclohexane] Hydrochloride To a stirred solution at room temperature of 5.0 g of (1'β,2'β)-2'-N-Methylaminoethylspiro[benzofuran-2(3H),1'-cyclohexane] hydrochloride in 250 ml. of methanol was added 3.2 g of NBS. The solution was stirred for 0.5 hours and concentrated in vacuo to a residue. The residue was taken up in 250 ml of $CH_2Cl_2$ and 200 ml of $H_2O$, and made basic with 2.5M NaOH. The separated aqueous phase was washed with 50 ml of $CH_2Cl_2$ and the combined organic layers are washed with brine and dried over $Na_2SO_4$. Concentration in vacuo gave 5.9 g (100% yield) of an oil. Purification of this material was afforded via formation of the hydrochloride salt. To this end, the oil was dissolved in 15 ml of absolute ethanol and 25 ml of ether. The ice cooled solution was acidified by the dropwise addition of a solution of ether saturated with hydrogen chloride. The addition of more ether produced a solid salt which was filtered and dried to give 4.3 g (67% yield) of crude hydrochloride salt. Two recrystallizations from ethanol/ether provided 2.0 g (31% yield) of (1'β,2'β)-2'-N-Methylaminoethylspiro[5-bromobenzofuran-2(3H),1'-cyclohexane] Hydrochloride, m.p. 189°-191° C.

ANALYSIS

Calculated for $C_{16}H_{22}BrNO \cdot HCl$: 53.28%C, 6.43%H, 3.88%N,
Found: 53.19%C, 6.27%H, 3.67%N.

EXAMPLE 65

(1'β,2'β)-2'-N-Methylaminoethylspiro[5-iodobenzofuran-2(3H), 1'-cyclohexane] Hydrochloride The procedure of Example 31 was repeated except that (1'β,2'β)-2'-N-methylaminoethylspiro[benzofuran-2(3H),1'-cyclohexane] was employed to obtain (1'β,2'β)-2'-N-methylaminoethylspiro[5-iodobenzofuran-2(3H),1'-cyclohexane]hydrochloride.

EXAMPLE 66

(1'β,2'β)-2'-N-Ethoxycarbonyl-N-methylaminoethylspiro[benzofuran-2(3H),1'-cyclohexane]

The procedure of Example 60 was repeated except that (1'β,2'β)-2'-N-methylaminoethylspiro[benzofuran-2(3H)-1'-cyclohexane] was employed to obtain (1'β,2'β)-2'-N-ethoxycarbonyl-N-methylaminoethylspiro[benzofuran-2(3H),1'-cyclohexane].

EXAMPLE 67

(1'β,2'β)-2'-N-Ethoxycarbonyl-N-methylaminoethylspiro[5-chlorobenzofuran-2(3H),1'-cyclohexane]

The procedure of Example 60 was repeated except that (1'β,2'β)-2'-N-methylaminoethylspiro[5-chlorobenzofuran-2(3H),1'-cyclohexane] was employed to obtain (1'β,2'β)-2'-N-Ethoxycarbonyl-N-methylaminoethylspiro[5-chlorobenzofuran-2(3H),1'-cyclohexane].

EXAMPLE 68

(1'β,2'β)-2'-Dimethylaminoethylspiro[benzofuran-2(3H),1'-cyclohexane] Hydrochloride The procedure of Example 62 was repeated except that (1'β,2'β)-2'-N-ethoxycarbonyl-N-methylaminoethylspiro[benzofuran-2(3H),1'-cyclohexane] was employed to obtain (1'β,2'β)-2'-Dimethylaminoethylspiro[benzofuran-2(3H),1'-cyclohexane] Hydrochloride.

EXAMPLE 69

(1'β,2'β)-2'-Dimethylaminoethylspiro[5-chlorobenzofuran-2(3H),1'-cyclohexane] hydrochloride The procedure of Example 62 was repeated except that (1'β,2'β)-2'-N-ethoxycarbonyl-N-methylaminoethylspiro[5-chlorobenzofuran-2(3H),1'-cyclohexane] was employed to obtain (1'β,2'β)-2'-Dimethylaminoethylspiro[5-chlorobenzofuran-2(3H), 1'-cyclohexane] hydrochloride, m.p. 217°-219°

EXAMPLE 70

(1'β,2'β)-2'-Dimethylaminoethylspiro[5-bromobenzofuran-2(3H), 1'-cyclohexane] hydrochloride The procedure of Example 50 was repeated except that (1'β,2'β)-2'-Dimethylaminoethylspiro[benzofuran-2(3H),1'-cyclohexane] Hydrochloride was employed to obtain (1'β,2'β)-2'-Dimethylaminoethylspiro[5-bromobenzofuran-2(3H),1'-cyclohexane] hydrochloride.

EXAMPLE 71

(1'β,2'β)-2'-Dimethylaminoethylspiro[5-iodobenzofuran-2(3H), 1'-cyclohexane] Hydrochloride The procedure of Example 31 was repeated except that (1'β,2'β)-2'-dimethylaminoethylspiro[benzofuran-2(3H),1'-cyclohexane] Hydrochloride was employed to obtain (1'β,2'β)-2'-dimethylaminoethylspiro[5-iodobenzofuran-2(3H),1'-cyclohexane] hydrochloride.

We claim:
1. A compound of the formula

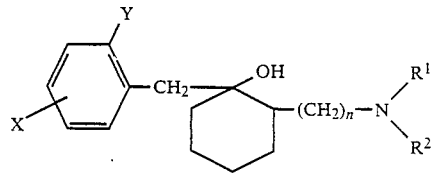

where X is hydrogen and halogen, and Y is halogen, halogen being any of fluorine, chlorine, bromine and iodine; n is an integer of 0 or 1; and $R^1$ and $R^2$ are each independently hydrogen and alkyl of 1 to 3 carbons and the stereoisomers thereof.

2. A compound as defined in claim 1 wherein n is 0.

3. The compound as defined in claim 1 which is 1-(2-fluorobenzyl)-2-dimethylaminocyclohexan-1-ol.

4. The compound as defined in claim 1 which is cis-1-(2-fluorobenzyl)-2-dimethylaminocyclohexan-1-ol.

5. The compound as defined in claim 1 which is 1-(5-chloro-2-fluorobenzyl)-2-dimethylaminocyclohexan-1-ol.

6. The compound as defined in claim 1 which is cis-1-(5-chloro-2-fluorobenzyl)-2-dimethylaminocyclohexan-1-ol.

7. The compound as defined in claim 1 wherein n is 1.

8. The compound as defined in claim 7 which is 2-(dimethylaminomethyl)-1-(2-fluorobenzyl)cyclohexan-1-ol.

9. The compound as defined in claim 7 which is cis- or trans-2-(dimethylaminomethyl)-1-(2-fluorobenzyl) cyclohexan-1-ol.

10. The compound as defined in claim 7 which is 1-(2,5-difluorobenzyl)-2-(dimethylaminomethyl) cyclohexan-1-ol.

11. The compound as defined in claim 7 which is cis- or trans-1-(2,5-difluorobenzyl)-2-(dimethylaminomethyl) cyclohexan-1-ol.

12. The compound as defined in claim 7 which is 1-(4-chloro-2-fluorobenzyl)-2-(dimethylaminomethyl)-cyclohexan-1-ol.

13. The compound as defined in claim 7 which is cis- or trans-1-(4-chloro-2-fluorobenzyl)-2-(dimethylaminomethyl)cyclohexan-1-ol.

14. The compound as defined in claim 7 which is 1-(5-chloro-2-fluorobenzyl)-2-(dimethylaminomethyl)-cyclohexan-1-ol.

15. The compound as defined in claim 7 which is cis- or trans-1-(5-chloro-2-fluorobenzyl)-2-(dimethylaminomethyl)cyclohexan-1-ol.

16. The compound as defined in claim 7 which is 1-(6-chloro-2-fluorobenzyl)-2-(dimethylaminomethyl)-cyclohexan-1-ol.

17. The compound as defined in claim 7 which is cis- or trans-1-(6-chloro-2-fluorobenzyl)-2-(dimethylaminomethyl)cyclohexan-1-ol.

18. The compound as defined in claim 7 which is 1-(2-fluorobenzyl)-2-(diethylaminomethyl)cyclohexan-1-ol.

19. The compound as defined in claim 7 which is cis- or trans-1-(2-fluorobenzyl)-2-(diethylaminomethyl)cyclohexan-1-ol.

20. The compound as defined in claim 7 which is 1-(5-chloro-2-fluorobenzyl)-2-(diethylaminomethyl)cyclohexan-1-ol.

21. The compound as defined in claim 7 which is cis- or trans-1-(5-chloro-2-fluorobenzyl)-2-(diethylaminomethyl)cyclohexan-1ol.

22. The compound as defined in claim 7 which is 1-(2-fluorobenzyl)-2-(di-n-propylaminomethyl)cyclohexan-1-ol.

23. The compound as defined in claim 7 which is cis- or trans-1-(2-fluorobenzyl)-2-(di-n-propylaminomethyl)cyclohexan-1-ol.

24. The compound as defined in claim 7 which is 1-(5-chloro-2-fluorobenzyl)-2-(di-n-propylaminomethyl) cyclohexan-1-ol.

25. The compound as defined in claim 7 which is cis- or trans-1-(5-chloro-2-fluorobenzyl)-2-(di-n-propylaminomethyl)cyclohexan-1-ol.

* * * * *